(12) United States Patent
Knipe et al.

(10) Patent No.: US 6,399,354 B1
(45) Date of Patent: Jun. 4, 2002

(54) REPLICATION-COMPETENT VIRUS EXPRESSING A DETECTABLE FUSION PROTEIN

(75) Inventors: David M Knipe, Auburndale; Travis J. Taylor, Brookline; Elizabeth E. McNamee, Brighton, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/127,227

(22) Filed: Jul. 31, 1998

(51) Int. Cl.$^7$ .......................... C12N 7/01; C12N 15/62; C12N 5/10; C12N 15/38
(52) U.S. Cl. ............................... 435/235.1; 435/320.1; 435/325; 435/69.7; 530/350; 536/23.4
(58) Field of Search .......................... 435/235.1, 320.1, 435/325, 975, 69.7; 530/350; 536/23.72, 23.4; 424/199.1

(56) References Cited

U.S. PATENT DOCUMENTS

| | | | |
|---|---|---|---|
| 4,859,587 A | 8/1989 | Roizman | 435/68 |
| 5,288,641 A | 2/1994 | Roizman | 435/320.1 |
| 5,328,688 A | 7/1994 | Roizman | 424/205.1 |
| 5,658,724 A | 8/1997 | DeLuca | 435/5 |
| 5,665,362 A | 9/1997 | Inglis et al. | 435/5 |

FOREIGN PATENT DOCUMENTS

| | | |
|---|---|---|
| EP | 0277773 | 1/1988 |
| EP | 0453242 | 4/1991 |
| WO | WO89/09271 | 10/1989 |
| WO | WO92/05263 | 4/1992 |
| WO | WO94/01573 | 1/1994 |
| WO | WO94/03207 | 2/1994 |
| WO | WO94/03595 | 2/1994 |
| WO | WO94/21807 | 9/1994 |

OTHER PUBLICATIONS

Cruz et al (PNAS 93: 6286–6290, 1996).*
Gao et al (Journal of Virology 67:876–85, 1993).*
Stauber et al (Virology 213: 439–49, 1995).*
Phelan et al (Nat. Biotechnol. 16(5):440–3, May 1998).*
Loimas et al (Biotechniques 24(4):614–8, Apr. 1998).*
Gerdes et al (FEBS Letters 389:44–47, 1996).*
Lee et al (BBRC 233:288–292, 1997).*
Brideau et al (Journal of Virology 72(6):4560–4570, Jun. 1998).*
Jons et al (Journal of Virological Methods 66:283–292, 1997).*
Desai et al. (Journal of Virology 72(9):7563–7578, Sep. 1998).*
Shih, M.–F. et al., "Expression of hepatitis B virus S gene by herpes simplex virus type 1 vectors carrying α– and β–regulated gene chimeras,"*Proc. Natl. Acad. Sci. USA*, 81:5867–5870 (1984) .

Nguyen, L.H. et al., "Replication–Defective Mutants of Herpes Simplex Virus (HSV) Induce Cellular Immunity and Protect against Lethal HSV Infection," *J. Virol.*, 66(12):7067–7072 (1992).

Gao, M. and Knipe, D.M., "Genetic Evidence for Multiple Nuclear Functions of the Herpes Simplex Virus ICP8 DNA–Binding Protein," *J. Virol.* 63(12):5258–5267 (1989).

Cunningham, C. et al., "The UL13 virion protein of herpes simplex virus type 1 is phosphorylated by a novel. Virus––induced protein kinase,"*J. Gen. Virol.* 73:303–311 (1992).

Ali, M.A. et al., "Enhanced malignant transformation induced by expression of a distinct protein domain of ribonucleotide reductase large subunit from herpes simplex virus type 2," *Proc. Natl. Acad. Sci. USA*, 88:8257–8261 (1991).

Rice, S.A. and Knipe, D.M., "Genetic Evidence for Two Distinct Transactivation Functions of the Herpes Simplex Virus α Protein ICP27," *J. Virol.*, 64:1704–1715 (1990).

Rice, S.A. et al., "Herpes Simplex Virus Alpha Protein ICP27 Possesses Separable Positive and Negative Regulatory Activities," *J. Virol.*, 63:3399–3407 (1989).

Quinn, J.P. and McGeoch, D.J., "DNA sequence of the region in the genome of herpes simplex virus type 1 containing the genes for DNA polymerase and the major DNA binding protein," *Nucl. Acids Res.*, 13(22):8143–8163 (1985) .

Sacks, W.R. et al., "Herpes Simplex Virus Type 1 ICP27 is an Essential Regulatory Protein," *J. Virol.* 55(3):796–805 (1985).

Galloway, D.A. et al., "Small fragments of herpesvirus DNA with transforming activity contain insertion sequence–like structures," *Proc. Natl. Acid Sci. USA*, 81:4736–4740 (1984).

Weller, S.K. et al., "Genetic Analysis of Temperature–Sensitive Mutants Which Define the Gene for the Major Herpes Simplex Virus Type 1 DNA–Binding Protein," *J. Virol.*, 45(1):354–366 (1983).

Farrell, H. et al., "Vaccine potential of a herpes simples virus mutant lacking an essential glycoprotein," Abstract, *17th International Herpesvirus Workshop*, Edinburgh, Scotland, p. 378 (Aug. 1–7, 1992).

(List continued on next page.)

*Primary Examiner*—Mary E. Mosher
(74) *Attorney, Agent, or Firm*—Hamilton, Brook, Smith & Reynolds, P.C.

(57) ABSTRACT

The claimed invention embodies a replication competent virus that expresses a detectable fusion protein. Any viral protein can be used to construct the fusion protein and fused with a detectable protein, such as a fluorescent protein. The claimed invention also relates to method for screening viral resistant cells and methods for identifying anti-viral agents or agents the block expression of the viral protein.

24 Claims, 12 Drawing Sheets

OTHER PUBLICATIONS

McLean, L. et al., "Protective vaccination with a gH–deleted HSV–1 virus," *18th International Herpesvirus Workshop*, Pittsburgh, PA, p. C–71 (Jul. 25–30, 1993).

DeLuca, N.A. et al., "Isolation and Characterization of Deletion Mutants of Herpes Simplex Virus Type 1 in the Gene Encoding Immediate–Early Regulatory Protein ICP4," *J. Virol.*, 56(2):558–570 (1985).

Jayaraman, S. et al., "Exacerbation of Murine Herpes Simplex Virus–Mediated Stromal Keratitis by Th2 Type T Cells," *J. Immunol.*, 151(10):5777–5789 (1993).

Marchetti, M.E. et al., "A Temperature–Sensitive Mutation in a Herpes Simplex Virus Type 1 Gene Required for Viral DNA Synthesis Maps to Coordinates 0.609 through 0.614 in $U_L$," *J. Virol.*, 62(3):715–721 (1988).

Ligas, M.W. and Johnson, D.C., "A Herpes Simplex Virus Mutant in which Glycoprotein D Sequences are Replaced by β–Galactosidase Sequences Binds to but is Unable to Penetrate into Cells," *J. Virol.*, 62(5):1486–1494 (1988).

Farrel, H.E. et al., "Vaccine Potential of a Herpes Simplex Virus Type 1 Mutant with an Essential Glycoprotein Deleted," *J. of Virol.* 68(2):927–932 (1994).

Morrison, L.A. and Knipe, D.M., "Immunization with Replication–Defective Mutants of Herpes Simplex Virus Type 1: Sites of Immune Intervention in Pathogenesis of Challenge Virus Infection," *J. Virol.* 68:689–696 (1994).

Nguyen, L. et al., "Mechanism of Virus–Induced Ig subclass Shifts," *J. Immunol.* 152:478–484 (1994).

Fields, B.N. et al., "Field's Virology," Lippincot–Raven Publishers, Philadelphia, PA, Chapters 72 (1996).

Sambrook, et al., "Molecular Cloning: A Laboratory Manual," 2nd ED., Chapter 17 (1989).

* cited by examiner

| VIRUS | MOI | YIELD (PFU/ML)[a] | |
|---|---|---|---|
| | | VERO | S2 |
| ICP8-GFP | 3 | $9.8 \times 10^4$ | $1.5 \times 10^8$ |
| KOS 1.1 | 3 | $8.8 \times 10^8$ | $8.5 \times 10^8$ |
| ICP8-GFP | 20 | $4.6 \times 10^5$ | $6.6 \times 10^7$ |
| KOS 1.1 | 20 | $6.8 \times 10^8$ | $7.7 \times 10^8$ |

[a] Determined by plaque assay on S2 cells

FIG. 2

```
atg gag aca aag ccc aag acg gca acc acc atc aag gtc ccc ccc ggg    48
ccc ctg gga tac gtg tac gct cgc gcg tgt ccg tcc gaa ggc atc gag    96
ctt ctg gcg tta ctg tcg gcg cgc agc ggc gat gcc gac gtc gcc gtg   144
gcg ccc ctg gtc gtg ggc ctg acc gtg gag agc ggc ttt gag gcc aac   192
gta gcc gtg gtc gtg ggt tct cgc acg acg ggg ctc ggg ggt acc gcg   240
gtg tcc ctg aaa ctg acg cca tcg cac tac agc tcg tcc gtg tac gtc   288
ttt cac ggc ggc cgg cac ctg gac ccc agc acc cag gcc cca aac ctg   336
acg cga ctc tgc gag cgg gca cgc cgc cat ttt ggc ttt tcg gac tac   384
acc ccc cgg ccc ggc gac ctc aaa cac gag acg acg ggg gag gcg ctg   432
tgt gag cgc ctc ggc ctg gac ccg gac cgc gcc ctc ctg tat ctg gtc   480
gtt acc gag ggc ttc aag gag gcc gtg tgc atc aac aac acc ttt ctg   528
cac ctg gga ggc tcg gac aag gta acc ata ggc ggg gcg gag gtg cac   576
cgc ata ccc gtg tat ccg ttg cag ctg ttc atg ccg gat ttt agc cgg   624
gtc atc gcc gag ccg ttc aac gcc aac cac cga tcg atc ggg gag aat   672
ttt acc tac ccg ctt ccg ttt ttt aac cgc ccc ctc aac cgc ctc ctg   720
ttc gag gcg gtc gtg gga ccc gcc gcc gtg gca ctg cga tgc cga aac   768
gtg gac gcc gtg gcc cgc gcg gcc gcc cac ctg gcg ttt gac gaa aac   816
cac gag ggc gcc gcc ctc ccc gcc gac att acg ttc acg gcc ttc gaa   864
gcc agc cag ggt aag acc ccg cgg ggt ggg cgc gac ggc ggc ggc aag   912
ggc ccg gcg ggc ggg ttc gaa cag cgc ctg gcc tcc gtc atg gcc gga   960
gac gcc gcc ctg gcc ctc gag tct atc gtg tcg atg gcc gtc ttc gac  1008
gag ccg ccc acc gac atc tcc gcg tgg ccg ctg tgc gag ggc cag gac  1056
acg gcc gcg gcc cgc gcc aac gcc gtc ggg gcg tac ctg gcg cgc gcc  1104
gcg gga ctc gtg ggg gcc atg gta ttt agc acc aac tcg gcc ctc cat  1152
ctc acc gag gtg gac gac gcc ggt ccg gcg gac cca aag gac cac agc  1200
aaa ccc tcc ttt tac cgc ttc ttc ctc gtg ccc ggg acc cac gtg gcg  1248
gcc aac cca cag gtg gac cgc gag gga cac gtg gtg ccc ggg ttc gag  1296
ggt cgg ccc acc gcg ccc ctc gtc ggc gga acc cag gaa ttt gcc ggc  1344
gag cac ctg gcc atg ctg tgt ggg ttt tcc ccg gcg ctg ctg gcc aag  1392
atg ctg ttt tac ctg gag cgc tgc gac ggc ggc gtg atc gtc ggg cgc  1440
```

FIG. 6A

```
cag gag atg gac gtg ttt cga tac gtc gcg gac tcc aac cag acc gac    1488
gtg ccc tgc aac ctg tgc acc ttc gac acg cgc cac gcc tgc gta cac    1536
acg acg ctc atg cgc ctc cgg gcg cgc cat ccc aag ttc gcc agc gcc    1584
gcc cgc gga gcc atc ggc gtc ttc ggg acc atg aac agc atg tac agc    1632
gac tgc gac gtg ctg gga aac tac gcc gcc ttc tcg gcc ctg aag cgc    1680
gcg gac gga tcc gag acc gcc cgg acc atc atg cag gag acg tac cgc    1728
gcg gcg acc gag cgc gtc atg gcc gaa ctc gag acc ctg cag tac gtg    1776
gac gag gcg gtc ccc acg gcc atg ggg cgg ctg gag acc atc atc acc    1824
aac cgc gag gcc ctg cat acg gtg gtg aac aac gtc agg cag gtc gtg    1872
gac cgc gag gtg gag cag ctg atg cgc aac ctg gtg gag ggg agg aac    1920
ttc aag ttt cgc gac ggt ctg ggc gag gcc aac cac gcc atg tcc ctg    1968
acg ctg gac ccg tac gcg tgc ggg cca tgc ccc ctg ctt cag ctt ctc    2016
ggg cgg cga tcc aac ctc gcc gtg tat cag gac ctg gcc ctg agc cag    2064
tgc cac ggg gtg ttc gcc ggg cag tcg gtc gag ggg cgc aac ttt cgc    2112
aat caa ttc caa ccg gtg ctg cgg cgg cgc gtg atg gac atg ttt aac    2160
aac ggg ttt ctg tcg gcc aaa acg ctg acg gtc gcg ctc tcg gag ggg    2208
gcg gct atc tgc gcc ccc agc cta acg gcc ggc cag acg gcc ccc gcc    2256
gag agc agc ttc gag ggc gac gtt gcc cgc gtg acc ctg ggg ttt ccc    2304
aag gag ctg cgc gtc aag agc cgc gtg ttg ttc gcg ggc gcg agc gcc    2352
aac gcg tcc gag gcc gcc aag gcg cgg gtc gcc agc ctc cag agc gcc    2400
tac cag aag ccc gac aag cgc gtg gac atc ctc ctc gga ccg ctg ggc    2448
ttt ctg ctg aag cag ttc cac gcg gcc atc ttc ccc aac ggc aag ccc    2496
ccg ggg tcc aac cag ccg aac ccg cag tgg ttc tgg acg gcc ctc caa    2544
cgc aac cag ctt ccc gcc cgg ctc ctg tcg cgc gag gac atc gag acc    2592
atc gcg ttc att aaa aag ttt tcc ctg gac tac ggc gcg ata aac ttt    2640
att aac ctg gcc ccc aac aac gtg agc gag ctg gcg atg tac tac atg    2688
gca aac cag att ctg cgg tac tgc gat cac tcg aca tac ttc atc aac    2736
acc ctc acg gcc atc atc gcg ggg tcc cgc cgt ccc ccc agc gtg cag    2784
gcg gcg gcc gcg tgg tcc gcg cag ggc ggg gcg ggc ctg gag gcc ggg    2832
gcc cgc gcg ctg atg gac gcc gtg gac gcg cat ccg ggc gcg tgg acg    2880
tcc atg ttc gcc agc tgc aac ctg ctg cgg ccc gtc atg gcg gcg cgc    2928
```

FIG. 6B

```
ccc atg gtc gtg ttg ggg ttg agc atc agc aaa tac tac ggc atg gcc    2976
ggc aac gac cgt gtg ttt cag gcc ggg aac tgg gcc agc ctg atg ggc    3024
ggc aaa aac gcg tgc ccg ctc ctt att ttt gac cgc acc cgc aag ttc    3072
gtc ctg gcc tgt ccc cgg gcc ggg ttt gtg tgc gcg gcc tcg aac ctc    3120
ggc ggc gga gcg cac gaa agc tcg ctg tgc gag cag ctc cgg ggc att    3168
atc tcc gag ggc ggg gcg gcc gtc gcc agt agc gtg ttc gtg gcg acc    3216
gtg aaa agc ctg ggg ccc cgc acc cag cag ctg cag atc gag gac tgg    3264
ctg gcg ctc ctg gag gac gag tac cta agc gag gag atg atg gag ctg    3312
acc gcg cgt gcc ctg gag cgc ggc aac ggc gag tgg tcg acg gac gcg    3360
gcc ctg gag gtg gcg cac gag gcc gag gcc cta gtc agc caa ctc ggc    3408
aac gcc ggg gag gtg ttt aac ttt ggg gat ttt ggc tgc gag gac gac    3456
aac gcg acg ccg ttc ggc ggc ccg ggg gcc ccg gga ccg gca ttt gcc    3504
ggc cgc aaa cgg gcg ttc cac ggg gat gac ccg ttt ggg gag ggg ccc    3552
ccc gac aaa aag gga gac ctg acg ttg gat atg ctg aga ggg gtt ggg    3600
ggg tgg ggg aac cta gag tcg acc cgg gcg gcc gcc gcc acc atg agc    3648
aag ggc gag gaa ctg ttc act ggc gtg gtc cca att ctc gtg gaa ctg    3696
gat ggc gat gtg aat ggg cac aaa ttt tct gtc agc gga gag ggt gaa    3744
ggt gat gcc aca tac gga aag ctc acc ctg aaa ttc atc tgc acc act    3792
gga aag ctc cct gtg cca tgg cca aca ctg gtc act acc ttc acc tat    3840
ggc gtg cag tgc ttt tcc aga tac cca gac cat atg aag cag cat gac    3888
ttt ttc aag agc gcc atg ccc gag ggc tat gtg cag gag aga acc atc    3936
ttt ttc aaa gat gac ggg aac tac aag acc cgc gct gaa gtc aag ttc    3984
gaa ggt gac acc ctg gtg aat aga atc gag ttg aag ggc att gac ttt    4032
aag gaa gat gga aac att ctc ggc cac aag ctg gaa tac aac tat aac    4080
tcc cac aat gtg tac atc atg gcc gac aag caa aag aat ggc atc aag    4128
gtc aac ttc aag atc aga cac aac att gag gat gga tcc gtg cag ctg    4176
gcc gac cat tat caa cag aac act cca atc ggc gac ggc cct gtg ctc    4224
ctc cca gac aac cat tac ctg tcc acc cag tct gcc ctg tct aaa gat    4272
ccc aac gaa aag aga gac cac atg gtc ctg ctg gag ttt gtg acc gct    4320
gct ggg atc aca cat ggc atg gac gag ctg tac aag tga              4359
```

FIG. 6C

```
Met Glu Thr Lys Pro Lys Thr Ala Thr Thr Ile Lys Val Pro Pro Gly
1               5               10                  15
Pro Leu Gly Tyr Val Tyr Ala Arg Ala Cys Pro Ser Glu Gly Ile Glu
            20              25              30
Leu Leu Ala Leu Leu Ser Ala Arg Ser Gly Asp Ala Asp Val Ala Val
            35              40              45
Ala Pro Leu Val Val Gly Leu Thr Val Glu Ser Gly Phe Glu Ala Asn
    50              55              60
Val Ala Val Val Val Gly Ser Arg Thr Thr Gly Leu Gly Gly Thr Ala
65              70              75              80
Val Ser Leu Lys Leu Thr Pro Ser His Tyr Ser Ser Ser Val Tyr Val
            85              90                  95
Phe His Gly Gly Arg His Leu Asp Pro Ser Thr Gln Ala Pro Asn Leu
            100             105             110
Thr Arg Leu Cys Glu Arg Ala Arg Arg His Phe Gly Phe Ser Asp Tyr
            115             120             125
Thr Pro Arg Pro Gly Asp Leu Lys His Glu Thr Thr Gly Glu Ala Leu
    130             135             140
Cys Glu Arg Leu Gly Leu Asp Pro Asp Arg Ala Leu Leu Tyr Leu Val
145             150             155             160
Val Thr Glu Gly Phe Lys Glu Ala Val Cys Ile Asn Asn Thr Phe Leu
            165             170             175
His Leu Gly Gly Ser Asp Lys Val Thr Ile Gly Gly Ala Glu Val His
            180             185             190
Arg Ile Pro Val Tyr Pro Leu Gln Leu Phe Met Pro Asp Phe Ser Arg
            195             200             205
Val Ile Ala Glu Pro Phe Asn Ala Asn His Arg Ser Ile Gly Glu Asn
    210             215             220
Phe Thr Tyr Pro Leu Pro Phe Phe Asn Arg Pro Leu Asn Arg Leu Leu
225             230             235             240
Phe Glu Ala Val Val Gly Pro Ala Ala Val Ala Leu Arg Cys Arg Asn
            245             250             255
Val Asp Ala Val Ala Arg Ala Ala Ala His Leu Ala Phe Asp Glu Asn
            260             265             270
His Glu Gly Ala Ala Leu Pro Ala Asp Ile Thr Phe Thr Ala Phe Glu
            275             280             285
Ala Ser Gln Gly Lys Thr Pro Arg Gly Gly Arg Asp Gly Gly Gly Lys
    290             295             300
Gly Pro Ala Gly Gly Phe Glu Gln Arg Leu Ala Ser Val Met Ala Gly
305             310             315             320
Asp Ala Ala Leu Ala Leu Glu Ser Ile Val Ser Met Ala Val Phe Asp
            325             330             335
Glu Pro Pro Thr Asp Ile Ser Ala Trp Pro Leu Cys Glu Gly Gln Asp
            340             345             350
Thr Ala Ala Ala Arg Ala Asn Ala Val Gly Ala Tyr Leu Ala Arg Ala
            355             360             365
Ala Gly Leu Val Gly Ala Met Val Phe Ser Thr Asn Ser Ala Leu His
    370             375             380
Leu Thr Glu Val Asp Asp Ala Gly Pro Ala Asp Pro Lys Asp His Ser
385             390             395             400
Lys Pro Ser Phe Tyr Arg Phe Phe Leu Val Pro Gly Thr His Val Ala
            405             410             415
```

FIG. 7A

```
Ala Asn Pro Gln Val Asp Arg Glu Gly His Val Val Pro Gly Phe Glu
        420                 425                 430
Gly Arg Pro Thr Ala Pro Leu Val Gly Gly Thr Gln Glu Phe Ala Gly
        435                 440                 445
Glu His Leu Ala Met Leu Cys Gly Phe Ser Pro Ala Leu Leu Ala Lys
        450                 455                 460
Met Leu Phe Tyr Leu Glu Arg Cys Asp Gly Gly Val Ile Val Gly Arg
465                 470                 475                 480
Gln Glu Met Asp Val Phe Arg Tyr Val Ala Asp Ser Asn Gln Thr Asp
                485                 490                 495
Val Pro Cys Asn Leu Cys Thr Phe Asp Thr Arg His Ala Cys Val His
            500                 505                 510
Thr Thr Leu Met Arg Leu Arg Ala Arg His Pro Lys Phe Ala Ser Ala
        515                 520                 525
Ala Arg Gly Ala Ile Gly Val Phe Gly Thr Met Asn Ser Met Tyr Ser
        530                 535                 540
Asp Cys Asp Val Leu Gly Asn Tyr Ala Ala Phe Ser Ala Leu Lys Arg
545                 550                 555                 560
Ala Asp Gly Ser Glu Thr Ala Arg Thr Ile Met Gln Glu Thr Tyr Arg
                565                 570                 575
Ala Ala Thr Glu Arg Val Met Ala Glu Leu Glu Thr Leu Gln Tyr Val
            580                 585                 590
Asp Gln Ala Val Pro Thr Ala Met Gly Arg Leu Glu Thr Ile Ile Thr
        595                 600                 605
Asn Arg Glu Ala Leu His Thr Val Val Asn Asn Val Arg Gln Val Val
        610                 615                 620
Asp Arg Glu Val Glu Gln Leu Met Arg Asn Leu Val Glu Gly Arg Asn
625                 630                 635                 640
Phe Lys Phe Arg Asp Gly Leu Gly Glu Ala Asn His Ala Met Ser Leu
                645                 650                 655
Thr Leu Asp Pro Tyr Ala Cys Gly Pro Cys Pro Leu Leu Gln Leu Leu
            660                 665                 670
Gly Arg Arg Ser Asn Leu Ala Val Tyr Gln Asp Leu Ala Leu Ser Gln
        675                 680                 685
Cys His Gly Val Phe Ala Gly Gln Ser Val Glu Gly Arg Asn Phe Arg
        690                 695                 700
Asn Gln Phe Gln Pro Val Leu Arg Arg Arg Val Met Asp Met Phe Asn
705                 710                 715                 720
Asn Gly Phe Leu Ser Ala Lys Thr Leu Thr Val Ala Leu Ser Glu Gly
                725                 730                 735
Ala Ala Ile Cys Ala Pro Ser Leu Thr Ala Gly Gln Thr Ala Pro Ala
            740                 745                 750
Glu Ser Ser Phe Glu Gly Asp Val Ala Arg Val Thr Leu Gly Phe Pro
        755                 760                 765
Lys Glu Leu Arg Val Lys Ser Arg Val Leu Phe Ala Gly Ala Ser Ala
        770                 775                 780
Asn Ala Ser Glu Ala Ala Lys Ala Arg Val Ala Ser Leu Gln Ser Ala
785                 790                 795                 800
Tyr Gln Lys Pro Asp Lys Arg Val Asp Ile Leu Leu Gly Pro Leu Gly
                805                 810                 815
Phe Leu Leu Lys Gln Phe His Ala Ala Ile Phe Pro Asn Gly Lys Pro
            820                 825                 830
Pro Gly Ser Asn Gln Pro Asn Pro Gln Trp Phe Trp Thr Ala Leu Gln
        835                 840                 845
Arg Asn Gln Leu Pro Ala Arg Leu Leu Ser Arg Glu Asp Ile Glu Thr
        850                 855                 860
```

FIG. 7B

```
Ile Ala Phe Ile Lys Lys Phe Ser Leu Asp Tyr Gly Ala Ile Asn Phe
865                 870                 875                 880
Ile Asn Leu Ala Pro Asn Asn Val Ser Glu Leu Ala Met Tyr Tyr Met
                885                 890                 895
Ala Asn Gln Ile Leu Arg Tyr Cys Asp His Ser Thr Tyr Phe Ile Asn
            900                 905                 910
Thr Leu Thr Ala Ile Ile Ala Gly Ser Arg Arg Pro Pro Ser Val Gln
        915                 920                 925
Ala Ala Ala Ala Trp Ser Ala Gln Gly Gly Ala Gly Leu Glu Ala Gly
    930                 935                 940
Ala Arg Ala Leu Met Asp Ala Val Asp Ala His Pro Gly Ala Trp Thr
945                 950                 955                 960
Ser Met Phe Ala Ser Cys Asn Leu Leu Arg Pro Val Met Ala Ala Arg
                965                 970                 975
Pro Met Val Val Leu Gly Leu Ser Ile Ser Lys Tyr Tyr Gly Met Ala
                980                 985                 990
Gly Asn Asp Arg Val Phe Gln Ala Gly Asn Trp Ala Ser Leu Met Gly
            995                 1000                1005
Gly Lys Asn Ala Cys Pro Leu Leu Ile Phe Asp Arg Thr Arg Lys Phe
        1010                1015                1020
Val Leu Ala Cys Pro Arg Ala Gly Phe Val Cys Ala Ala Ser Asn Leu
1025                1030                1035                1040
Gly Gly Gly Ala His Glu Ser Ser Leu Cys Glu Gln Leu Arg Gly Ile
                1045                1050                1055
Ile Ser Glu Gly Gly Ala Ala Val Ala Ser Ser Val Phe Val Ala Thr
            1060                1065                1070
Val Lys Ser Leu Gly Pro Arg Thr Gln Gln Leu Gln Ile Glu Asp Trp
        1075                1080                1085
Leu Ala Leu Leu Glu Asp Glu Tyr Leu Ser Glu Glu Met Met Glu Leu
    1090                1095                1100
Thr Ala Arg Ala Leu Glu Arg Gly Asn Gly Glu Trp Ser Thr Asp Ala
1105                1110                1115                1120
Ala Leu Glu Val Ala His Glu Ala Glu Ala Leu Val Ser Gln Leu Gly
                1125                1130                1135
Asn Ala Gly Glu Val Phe Asn Phe Gly Asp Phe Gly Cys Glu Asp Asp
            1140                1145                1150
Asn Ala Thr Pro Phe Gly Gly Pro Gly Ala Pro Gly Pro Ala Phe Ala
        1155                1160                1165
Gly Arg Lys Arg Ala Phe His Gly Asp Asp Pro Phe Gly Glu Gly Pro
    1170                1175                1180
Pro Asp Lys Lys Gly Asp Leu Thr Leu Asp Met Leu Arg Gly Val Gly
1185                1190                1195                1200
Gly Trp Gly Asn Leu Glu Ser Thr Arg Ala Ala Ala Ala Thr Met Ser
                1205                1210                1215
Lys Gly Glu Glu Leu Phe Thr Gly Val Val Pro Ile Leu Val Glu Leu
            1220                1225                1230
Asp Gly Asp Val Asn Gly His Lys Phe Ser Val Ser Gly Glu Gly Glu
        1235                1240                1245
Gly Asp Ala Thr Tyr Gly Lys Leu Thr Leu Lys Phe Ile Cys Thr Thr
    1250                1255                1260
Gly Lys Leu Pro Val Pro Trp Pro Thr Leu Val Thr Thr Phe Thr Tyr
1265                1270                1275                1280
Gly Val Gln Cys Phe Ser Arg Tyr Pro Asp His Met Lys Gln His Asp
                1285                1290                1295
Phe Phe Lys Ser Ala Met Pro Glu Gly Tyr Val Gln Glu Arg Thr Ile
            1300                1305                1310
Phe Phe Lys Asp Asp Gly Asn Tyr Lys Thr Arg Ala Glu Val Lys Phe
        1315                1320                1325
                        FIG. 7C
```

Glu Gly Asp Thr Leu Val Asn Arg Ile Glu Leu Lys Gly Ile Asp Phe
                1330                1335                1340
Lys Glu Asp Gly Asn Ile Leu Gly His Lys Leu Glu Tyr Asn Tyr Asn
1345                1350                1355                1360
Ser His Asn Val Tyr Ile Met Ala Asp Lys Gln Lys Asn Gly Ile Lys
                1365                1370                1375
Val Asn Phe Lys Ile Arg His Asn Ile Glu Asp Gly Ser Val Gln Leu
            1380                1385                1390
Ala Asp His Tyr Gln Gln Asn Thr Pro Ile Gly Asp Gly Pro Val Leu
            1395                1400                1405
Leu Pro Asp Asn His Tyr Leu Ser Thr Gln Ser Ala Leu Ser Lys Asp
        1410                1415                1420
Pro Asn Glu Lys Arg Asp His Met Val Leu Leu Glu Phe Val Thr Ala
1425                1430                1435                1440
Ala Gly Ile Thr His Gly Met Asp Glu Leu Tyr Lys
                1445                1450

REPLICATION-COMPETENT VIRUS EXPRESSING A DETECTABLE FUSION PROTEIN

GOVERNMENT SUPPORT

The invention was supported, in whole or in part, by a grant CA26345 from Genetics of Herpesvirus Transformation. The Government has certain rights in the invention.

BACKGROUND OF THE INVENTION

Viruses play an important role in a person's health. Several viruses infect people for which no effective treatment plan exists. Examples of such viruses include herpesvirus, Human Immunodeficiency Virus (HIV) and the common cold. Finding effective anti-viral drugs depends on the ability to track the virus in a host or cell after the drug has been administered. Therefore, a need exists to be able to efficiently detect the presence or absence of a virus. A further need exists to develop screening methods for determining the efficacy of anti-viral agents or compounds. Another need exists to determine whether a cell is resistant to viral infection.

SUMMARY OF THE INVENTION

The invention embodies a fusion protein comprising a viral protein and a detectable protein. The viral protein and the detectable protein can be linked so that viral protein's native function is maintained. The detectable fusion protein can efficiently detect the presence, absence, or amount of viral DNA replication and, therefore, infection. The protein is thus a marker selected from a variety of viruses. Examples of such viruses are: the retrovirus (Human Immunodeficiency Virus (HIV)), the influenzavirus, the papillomavirus, the rhinovirus, and the herpesvirus (e.g., Herpes Simplex Virus-1 (HSV-1), Herpes Simplex Virus-2 (HSV-2), a Varicella-Zoster Virus, Epstein-Barr Virus, Cytomegalovirus, Human Herpesvirus-6, and Human Herpesvirus-7). In particular, a claimed invention embodies a viral protein from a Herpesvirus fused with a detectable protein (e.g., a fluorescent protein, or a protein that emits fluorescence upon excitation). An example of a fluorescent protein which can be used in the invention is a green fluorescent protein (GFP). In particular, a preferred embodiment utilizes the HSV ICP8 viral protein fused with a fluorescent protein, such as ICP8-GFP. In another embodiment, the invention pertains to antibodies which selectively bind to such a fusion protein, and plasmids or vectors that encode the fusion proteins, as described herein.

The invention also encompasses a virus that comprises a nucleic acid which expresses the claimed fusion protein. The recombinant virus which expresses the fusion protein is generally able to perform functions similar to a corresponding wild-type virus. The virus is preferably replication competent and in the case of the Herpesvirus able to form replication compartments, a "factory" where DNA synthesis takes place and possibly where virions are assembled. The invention embodies a virus which can express a fusion protein that consists of a viral protein and a fluorescent protein. In particular, the claimed invention relates to a virus that expresses ICP8-GFP.

The invention also includes methods for determining whether a cell is virus resistant. Such a method includes infecting the cell to be tested with a virus that expresses the fusion protein, and then detecting the presence or absence of the fusion protein. A fusion protein comprising a fluorescent protein can be identified by detecting the amount of fluorescence emitted by the protein. The invention also pertains to a method for identifying an anti-viral agent or an agent that blocks infection or other viral function and, thus, the expression of the fusion protein. Such a method can involve infecting a host cell with a virus as described herein and subjecting a host cell to the agent to be tested, and then detecting the presence of the fusion protein. A decrease in the amount of fusion protein indicates that the agent can be an anti-viral agent or an agent that blocks the expression of the fusion protein. Again, when the fusion protein contains a fluorescent protein, the amount of virus present can be detected by the amount of fluorescence emitted by the fusion protein. Another way of detecting the amount of herpesviral replication present can be by determining the amount of replication compartment formation.

The invention also embodies identifying an agent that reduces infection of a virus in vivo. Such a method includes infecting a mammal with a virus that expresses the fusion protein and then subjecting the mammal with the agent to be tested. One then removes a portion of the infected tissue and detects the amount of fusion protein that is produced. A decrease in the amount of fusion protein indicates that the agent is effective in treating the virus. Similarly, the invention can be used to assay for virus resistant cells.

The claimed invention specifically embodies a fusion protein having a herpesviral protein (e.g., ICP8), and the fluorescent protein (e.g., a green fluorescent protein (GFP)). The ICP8-green fluorescent protein is embodied by the claimed invention and its amino acid sequence is referred to herein as SEQ ID NO: 2. The claimed invention also relates to the nucleic acid sequence that encodes the ICP8-GFP fusion protein and is referred to herein as SEQ ID NO: 1.

The invention also relates to a kit that comprises a virus which is capable of expressing the fusion protein, as described herein. The kit can further comprise a complementing cell line or one that expresses the corresponding wild-type viral protein (e.g., S-2) and/or a cell line into which the virus can be transfected (e.g., Vero cell).

BRIEF DESCRIPTION OF THE DRAWINGS

The foregoing features and advantages of the invention will be apparent from the following more particular description of the preferred embodiments of the invention, as illustrated in the accompanying figures. Emphasis is placed on illustrating the principles of the invention.

FIG. 2 shows the single cycle growth of the 8GFP recombinant virus, as determined by a plaque assay on S2 cells.

FIG. 3A shows mock infected cells. FIG. 3B shows S2 cells at 7.5 hours post infection. FIG. 3C shows S2 cells with 400 ug/ml PAA at 7.5 hours post-infection.

FIG. 4A is at 400× magnification of infected cornea and FIG. 4B shows the phase at the same magnification.

FIGS. 5A–5D are panels at 1000× magnification.

FIGS. 6A–6C show the nucleic acid sequence that encodes for the ICP8-GFP fusion protein (e.g., SEQ ID NO: 1).

FIGS. 7A–7D show the amino acid sequence of the ICP8-GFP fusion protein (e.g., SEQ ID NO: 2).

DETAILED DESCRIPTION OF THE INVENTION

Figure 1:
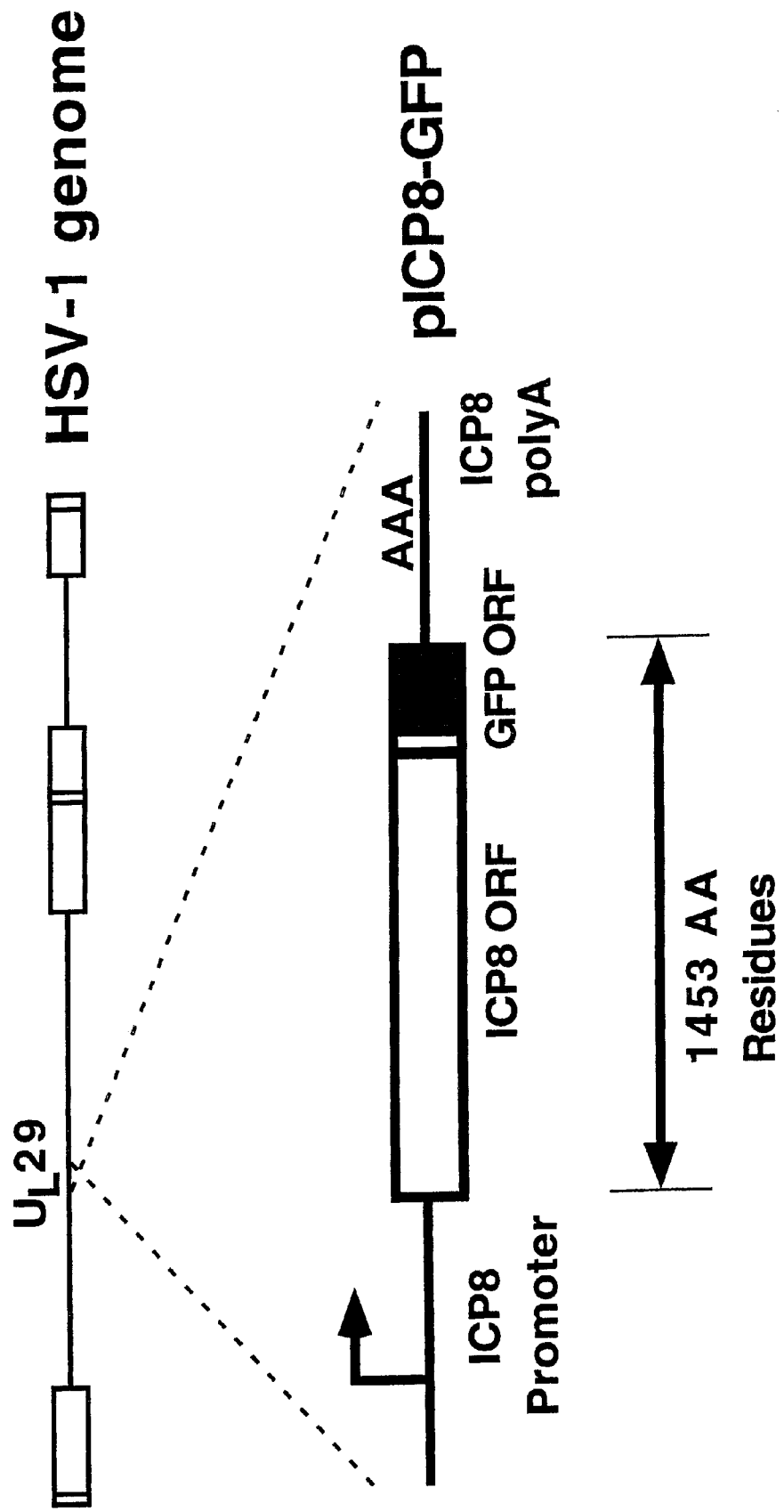
FIG. 1 is a diagram illustrating the pICP8-GFP. The figure maps the residues of the ICP8-GFP sequence.

The invention embodies a fusion protein comprising a viral protein and a detectable protein. The fusion protein generally maintains some function of the native viral protein, however, the function can be maintained to a lesser or greater extent. The specific function of the protein to be selected is not generally critical.

The viral protein can be derived from a variety of viruses. Such viruses include the retrovirus (e.g., Human Immunodeficiency virus (HIV)), influenzavirus, rhinovirus, papillomavirus and herpesvirus. A preferred embodiment of the invention encompasses a viral protein from a herpesvirus. Examples of herpesviruses are Herpes Simplex Virus-1 (HSV-1), Herpes Simplex Virus-2 (HSV-2), Varicella-Zoster Virus (VZV), Epstein-Bar Virus (EBV), Cytomegalovirus (CMV), Human Herpesvirus-6 (HHV-6), and Human Herpesvirus-7 (HHV-7). In particular, a preferred embodiment of the invention includes a viral particle from the Herpes Simplex Virus (HSV). An embodiment includes the HSV ICP8 viral protein as a fusing partner.

Another portion of the fusion protein, as described above, is the detectable protein. Preferably, the protein can be detected visually or fluorescently. The detectable protein can be detected automatically or may require excitation. A preferred embodiment of the invention employs a fluorescent protein as the detectable protein. The fluorescent protein is defined as a protein that emits fluorescence upon excitation. Therefore, a preferred embodiment of the claimed invention is a Herpesvirus protein fused with a fluorescent protein. An example of a fluorescent protein that is utilized by the claimed invention is the green fluorescent protein (GFP). In particular, an embodiment of the claimed invention is a fusion protein linking ICP8 and GFP, referred to as "ICP8-GFP." ICP8-GFP has an amino acid sequence, SEQ ID NO:2, and is shown in FIGS. 7A–7D. The invention also encompasses the nucleic acid sequence that encodes for ICP8-GFP, designated as SEQ ID NO:1, shown in FIGS. 6A–6C.

The term "protein" is intended to encompass fragments, analogs or derivatives of the native protein. Generally, the fragment, analog or derivative maintains at least one function. The claimed invention is intended to embody the various functional domains of the fusion protein, as described herein. Analogous amino acid sequences generally mean amino acid sequences with sufficient identity to the native protein amino acid sequence so as to possess the biological activity of the fusion protein. For example, an analogous peptide can be produced with "silent" changes in amino acid sequence wherein one, or more, amino acid residues differ from the amino acid residues of the fusion protein, yet still possess substantially the same biological activity of the native. Examples of such differences include additions, deletions or substitutions of residues of the amino acid sequence of the fusion protein. Also encompassed by the claimed invention are analogous polypeptides that exhibit greater, or lesser, biological activity of the fusion protein.

The claimed invention also encompasses biologically active polypeptide fragments of the fusion protein described herein. Such fragments can include only a part of a full length amino acid sequence of fusion protein and yet possess the same function, possibly to a lesser or greater extent. For example, polypeptide fragments comprising deletion mutants of the fusion protein can be designed and expressed by well known laboratory methods. Such polypeptide fragments can be evaluated for biological activity.

Forms of Nucleic Acid that Encodes the Fusion Protein

The claimed invention encompasses isolated nucleic acid sequences encoding the fusion protein, and fragments of nucleic acid sequences encoding biologically active portions of the fusion protein.

Fragments of the nucleic acid sequences described herein are useful as probes to detect the presence of the nucleic acid that encodes the fusion protein. Also encompassed by the claimed invention are nucleic acid sequences, DNA or RNA, which are substantially complementary to the DNA sequences encoding the fusion protein, and which specifically hybridize with the DNA sequences under conditions of stringency known to those of skill in the art. Substantially complementary means that the nucleic acid need not reflect the exact sequence of the fusion protein DNA, but are sufficiently similar in sequence to permit hybridization with the fusion protein DNA under stringent conditions. Conditions for stringency are described in e.g., Ausubel, F. M., et al., Current Protocols in Molecular Biology, (Current Protocol, 1994).

The invention also provides vectors or plasmids containing the nucleic acid that encodes for the fusion protein. Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989), the teachings of which are incorporated herein by reference.

The nucleic acid molecule can be incorporated or inserted into the host cell by known methods. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example. Once the nucleic acid is incorporated into the host cell, the cell can be maintained under suitable conditions for expression and recovery of fusion protein. Generally, the cells are maintained in a suitable buffer and/or growth medium or nutrient source for growth of the cells and expression of the gene product(s). The growth media are not critical to the invention, are generally known in the art and can include sources of carbon, nitrogen and sulfur. Examples include Luria broth, Superbroth, Dulbecco's Modified Eagles Media (DMEM), RPMI-1640, M199 and Grace's insect media. The growth Media may contain a buffer, the selection of which is not critical to the invention. The pH of the buffered media can be selected and is generally one tolerated by or optimal for growth for the host cell.

A Virus that Expresses the Fusion Protein

The invention relates to a virus comprising a nucleic acid which expresses the fusion protein, as described herein. The virus generally corresponds to the viral protein used in the fusion protein. For example, if a viral protein from HSV-1 is fused with a fluorescent protein, then the HSV-1 virus can be used to express this fusion protein. A virus that expresses the fusion protein is generally replication competent. The term, "replication competent," is defined as the ability for the virus to grow and replicate viral DNA and, optionally, in normal cultured cells (e.g., a Herpesvirus that grows in a Vero cell) infect or spread to new cells. This can include the ability to make infectious viral particles and infect new cells. Specifically, for herpesviruses, the virus can include an ability to form replication compartments. The formation of replication compartments refers to a factory where DNA synthesis takes place, and possibly the area where virions are assembled. A virus that expresses the fusion protein and maintains functions similar to the corresponding wild type virus or maintains one or more "viral functions" also generally includes the ability for the virus to undergo attachment, transcription, DNA replication, and/or assembly including the ability to infect a host cell. The claimed virus that expresses the fusion protein should exhibit at least one of these functional characteristics, although these functional characteristics may independently occur to a lesser or greater extent. In particular, a preferred embodiment of the invention is a Herpesvirus that expresses the fusion protein (e.g., a fusion protein containing a Herpesvirus protein fused with a detectable protein). Specifically, the claimed invention embodies a virus that expresses the ICP8-GFP fusion protein. This virus is referred to as the "8GFP virus."

The invention also pertains to a kit comprising the virus which is described herein. The kit may also include a cell line that is capable of complementing one or more viral proteins. For example, the 8GFP virus may be accompanied by S-2 cells, a complementing cell line which expresses HSV ICP8. A kit may further comprise a cell line into which the virus may be transfected, e.g., a vero cell.

Construction Of The Fusion Gene And A Virus That Can Express The Fusion Protein Construction of a gene that encodes a fusion protein requires routine methods and techniques. Ausubel, F. M., et al., "Current Protocols in Molecular Biology," John Wiley & Sons (1998); Sambrook, et al., "Molecular Cloning: A Laboratory Manual" 2nd Edition (1989). A skilled artisan must link two nucleotide sequences so that the open reading frame is maintained. Using the appropriate restriction sites, one can clone the nucleic acid sequence of one of the proteins to be fused (e.g., the detectable protein) into a vector. Subsequently, the nucleic acid sequence of the second protein (e.g., the viral protein) may also be cloned into the same vector in a manner to maintain the open reading frame and link the nucleotide sequences of both proteins. This is done by appropriately utilizing restriction sites and enzymes. Thereafter, PCR is used to amplify the sequence. The reaction is then digested and a sufficient amount of sequence is transfected into an expression system (e.g., $E.\ coli$).

The detectable protein may be fused or linked to either the amino terminus or the carboxyl terminus of the viral protein. A preferred embodiment of the claimed invention pertains to a Herpesvirus viral protein fused with a fluorescent protein. In particular, the preferred embodiment of the invention relates to the ICP8-GFP fusion protein. The ICP8 viral protein is derived from an a herpesvirus, such as HSV-1 virus. In this case, the fluorescent protein was linked to the carboxyl terminus of the viral protein, which allowed the viral protein (e.g., ICP8) to maintain its function (e.g., its role in viral replication). Other herpesvirus proteins which can be used are described in Field's Virology:(Vol 1 & 2), Fields, Bernard N., et al., editor, Lippincot-Raven Publishers, Philadelphia, Pa. (1996). the contents of which are incorporated herein by reference in their entirety. A description of how to construct the fusion protein is discussed throughout the specification and in particular in Example 1. Although Example 1 illustrates the specific instructions of how to make the ICP8-GFP fusion protein, these methods and materials can be adapted to make the fusion protein from any viral protein and/or detectable protein.

Construction Of A Virus That Expresses The Fusion Protein

Construction of a virus that expresses a fusion protein as described herein, also requires well known molecular cloning techniques. Ausubel, F. M., et al., "Current Protocols in Molecular Biology," John Wiley & Sons (1998); Sambrook, et al., "Molecular Cloning: A Laboratory Manual" 2nd Edition (1989). A skilled artisan can combine the fusion protein's nucleic acid with a corresponding mutated virus. This virus is mutated so that viral protein that was used for the fusion protein, has been altered or otherwise nonfunctional or ineffective. In the preferred embodiment, the inventors combined the ICP8-GFP fusion protein with a virus that expressed a truncated form of ICP8. The defective virus and the fusion protein were cotransfected into a complementing cell line, a cell line which expresses the native viral protein (e.g., ICP8). The cells are then grown and cultured. The cells are screened by detecting the detectable protein. The preferred embodiment of the claimed invention includes a Herpesvirus that can express a Herpesvirus protein fused with a fluorescent protein. Accordingly, in constructing such a virus, the presence of the virus was assayed by detecting the emission of fluorescence using an ultraviolet light.

Another preferred embodiment of the invention is the 8GFP virus, which expresses the ICP8-GFP fusion protein. This virus was constructed using a HD-2 replication defective mutant virus. HD-2 makes an altered, nonfunctional form of ICP8, truncated ICP8. This mutant virus was cotransfected with the nucleic acid that encodes the ICP8-GFP fusion protein. One can make a virus in which an altered viral protein is expressed using known methods in the art and methods detailed in the following patent applications: Ser. Nos. 09/034,464, 08/903,830, 08/278,601, 08/179,106, and 07/922,912, entitled "Herpesvirus Replication Defective Mutants", the teachings of which are incorporated herein by reference in their entirety. Example 1 describes in more detail the methods and materials necessary to construct the 8GFP virus. The methods described in Example 1 can be modified and adapted by methods known in the art to make other viruses that express a fusion protein, including other Herpesviruses, retroviruses, papillomaviruses, influenzaviruses, and Rhinoviruses.

Applications Of A Replication Competent Virus That Expresses A Fusion Protein The novelty of the claimed invention lies with the ability to readily and easily detect a virus that can undergo similar functions of the corresponding wild type virus. Such a virus enables a skilled artisan to more easily study the virus and drugs that may impact the virus's ability to infect a host cell or replicate. The claimed invention embodies such a virus. A preferred embodiment is a Herpesvirus that is detectable by virtue of the expression of a detectable fusion protein, as described herein.

This virus allows a skilled artisan to screen for virus resistant cells and identify antiviral drug targets. The replication competent virus also enables one to assay for antiviral agents or compounds that block expression of the detectable protein or its assembly into replication compartment in cultured cells. Furthermore, this virus allows for the assessment of the efficiency of antiviral agents or immunological reagents in vivo.

Methods for screening infection in cells involve contacting the virus with the cell under conditions that are sufficient for the virus to infect the cell. Determining such conditions are matters that are routine to a skilled artisan. A skilled artisan can detect the presence or absence of the fusion protein. In the preferred embodiment, the detectable protein is a fluorescent protein. Therefore, detecting the absence or presence of the fusion protein can involve detecting the amount of fluorescence emitted by the fusion protein. A cell that contains the fusion protein will emit fluorescence, whereas a cell that does not contain the fusion protein will not emit fluorescence. A cell which does not emit fluorescence likely does not contain the virus and is, therefore, not infected. Contrarily, a cell that contains the fusion protein also contains the virus, and is, therefore, infected. These cells can be sorted with a fluorescence activated cell sorter. The cells that are resistant can be grown and cultured, a process that can be repeated more than once. Repetition of the process ensures that you have obtained a virus resistant cell and its progeny also provides virus resistant cells. Another approach for detecting virus resistant cells involves selecting for cells which survive. After selecting surviving cells, a skilled artisan can measure the fluorescence emitted from the cells. Cells which survive and do not emit fluorescence are considered to be virus resistant cells. The assay can be used, therefore, to detect virus-resistant and/or virus-susceptible cells.

The methods can be used for the identification of antiviral drug targets, antiviral agents or compounds, and/or agents that block the expression of the fusion protein. These methods are performed in a similar manner described above, adding the agent to be tested. Preferably, the methods involve contacting a virus, as described herein, with the cell, under conditions that are sufficient to allow the virus to infect the cell. The agent to be tested can be added with, before or after the addition of the virus or cell. The amount of fusion protein or virus present can be detected in a number of ways. In the preferred embodiment, wherein the detectable protein is a fluorescent protein, the fusion protein can be detected by detecting the amount of fluorescence emitted. A decrease in the amount or absence of fluorescence indicates that the agent has antiviral activity. The fluorescence can be measured against a control (e.g., a virus that expresses the fusion protein without being subjected to the agent) or compared to an appropriate standard for the assay. Another way for identifying an antiviral agent or an agent that blocks the expression of the fusion protein is by analyzing the replication compartment formation by the virus. A lack of replication compartment formation indicates interference with the viral cycle, such as occurs in blocking DNA replication or decreasing the assembly of virions.

Another way of identifying an antiviral agent or an agent that blocks expression of the fusion protein is by subjecting the cells which have been infected with the virus and allowing the virus to spread in the presence of the agent. A skilled artisan can then detect the spread of fluorescence emitted by the cells. Again, a decrease in fluorescence indicates that the agent is an antiviral agent or one that blocks expression of the fusion protein.

A replication competent virus that expresses a detectable fusion protein can also be used in the methods for identify an agent that reduces the infection of a virus in vivo. The method involves infecting a mammal with the virus that expresses the fusion protein and then subjecting the mammal with the agent to be tested. A portion of the infected tissue can then be removed and analyzed. A skilled artisan can detect the amount of the fusion protein that is expressed by the virus as described herein. Again, a decrease in the amount of fluorescence indicates that the agent can reduce infection of the virus in vivo.

The claimed invention embodies any antiviral agent, as identified by the methods described herein. An antiviral agent is defined as a compound, drug, immunological reagent or composition, that can reduce or cease the viral infection, or symptoms that are associated with viral infection.

EXEMPLIFICATION

EXAMPLE 1

Replication-Competent Herpesvirus Expressing a Fluorescent Nuclear Protein

This invention reports a replication-competent herpes simplex virus that expresses a viral DNA replication protein fused to and tagged with the green fluorescent protein (GFP). The fluorescent fusion protein enters the nucleus and assembles into replication compartments. Among other applications, this virus can be used as: 1) a means to screen for virus-resistant cells and to identify new antiviral drug targets, 2) an assay for antiviral compounds that block expression of the fluorescent fusion protein or its assembly into replication compartments in cultured cells, or 3) an assay for antiviral compounds or immunological reagents that reduce viral infection and spread in experimental animal systems such as the mouse cornea.

Construction of an ICP8-GFP Fusion Gene

A 732 base pair NotI fragment containing the green fluorescent protein (GFP) open reading frame from pGreen-Lantern (Gibco-BRL) was cloned into the NotI site of $pCI_{AA}$flII creating $pCI_{AA}$-GFP. A 3.8-kb EcoRI/AvrII fragment containing the entire ICP8 ORF from pSV8.2 was cloned into the EcoRI and XbaI sites of $pCI_{AA}$-GFP. The fusion protein ORF was generated by mutating the ICP8 stop codon via PCR mediated site-directed mutagenesis with Pfu DNA polymerase (Stratagene) (one cycle 95° C. 2 min; twelve cycles 95° C. 30 s, 55° C. 1 min, 68° C. 18 min). The two primers used for changing the stop codon to an arginine residue were 5'CAACCCCTCTCAGCATATCCAACG-3' (SEQ ID NO.: 3)(sense) and 5'CGTTGGATATGCTGAGAGGGGTTG-3' (SEQ ID NO.: 4)(antisense) (Gibco-BRL). The nucleotide that was altered is underlined. After PCR amplification, the reaction was digested with DpnI, and 1 μl of the reaction was used to transform E. coli. The fusion protein consists of 1453 amino acid residues: 1196 residues from ICP8, 18 residues in the linker region between ICP8 and GFP, and 239 residues from GFP (FIG. 1). The predicted size of the ICP8-GFP fusion protein is approximately 160 kiloDaltons (kDa).

The EcoRI site 172 nucleotides upstream from the ICP8 gene ATG was filled in and converted to a BgIII restriction site by the insertion of a 12 base pair oligonucleotide linker (5'-GGAAGATCTTCC-3')(SEQ ID NO.: 5)) (NEB). The HpaI site 147 nucleotides downstream of the GFP coding sequence was also converted to a BgIII restriction site with the same oligonucleotide linker. The resulting 4.7-kb BgIII fragment was cloned into the BgIII site of pICP8PA, which contains the ICP8 promoter and poly A sequences, creating pICP8-GFP (see FIG. 1). The ICP8 promoter requires other viral proteins for expression so, upon transfection of Vero cells with pICP8-GFP, the cells with not efficiently express the ICP8-GFP fusion protein unless subsequently superinfected with HSV.

Isolation of a Recombinant HSV-1 Expressing the ICP8-GFP Fusion Protein

To create an ICP8-GFP expressing virus via homologous recombinants (FIG. 1), linearized pICP8-GFP and HD-2 viral DNA were co-transfected via the calcium phosphate method into the ICP8 complementing cell line V827. HD-2 is a replication defective virus that expresses a truncated ICP8 fused to the lacZ ORF (ICP8-lacZ). The DNA was transfected with various molar ratios of HD-2 viral DNA to plasmid DNA (1:10, 1:15, 1:20) and brought to a total of 16 µg DNA with salmon sperm DNA. An equal volume of 2× HBS pH 7.05 (270 mM NaCl, 10 mM KCl, 1.4 mM Na2HPO4, 2% dextrose, 42 mM HEPES) was added to the DNA. The volume was brought up to 600 µl with 1× HBS, and then 40 µl of 2.0 M CaCl2 was added dropwise. The tubes were mixed gently and incubated at room temperature for 15 min. The precipitate was then added to T25 flasks of subconfluent V827 cells and incubated at room temperature for 30 min, after which 5 ml of DMEM+10% FBS was added and the flasks were placed at 37° C. On the following day, the cells were washed twice and overlaid with new media. Four days later, the cells were harvested by adding 2.5-ml sterile milk and freeze-thawing twice. The lysate was sonicated on ice for 30 seconds on/30 seconds off three times. The lysate was then serially diluted and plated on V827 cells. An inverted, fluorescent Nikon microscope equipped with a FITC filter set was used to screen for fluorescent plaques under UV light. A glowing plaque was chosen and plaque purified twice more on V827 cells for the preparation of a stock of the ICP8-GFP virus.

Characterization of the ICP8-GFP Recombinant Virus

To confirm that the recombinant ICP8-GFP virus expressed the correct fusion protein, labeled cell extracts were analyzed by SDS-PAGE. Briefly, Vero cell monolayers were infected at a multiplicity of infection (moi) of 10 with the recombinant ICP8-GFP virus, wildtype KOS 1.1 virus, or the parental HD-2 virus. The cells were labeled for 30 minutes at 4, 6, 8, 10, or 12 hours post-infection and subsequently harvested in lysis buffer (60 mM Tris-Cl, pH 7.5, 2% SDS, 20% glycerol, 0.5% BME, 2 µg/ml aprotinin, 5 µg/ml leupeptin). Labeled, infected cell proteins were separated by SDS-PAGE. The gel was fixed, dried, and exposed to Kodak Bio-Max MR film. The wildtype ICP8 (128 kDa) and the HD-2 ICP8-lacZ (145 kDa) proteins were readily detected in the lanes corresponding to KOS 1.1 and HD-2 infections, respectively. Neither wildtype ICP8 nor ICP8-lacZ proteins could be detected in the lanes corresponding with ICP8-GFP virus infection, rather, a new band at the predicted size (160 kDa) of the ICP8-GFP fusion protein was observed. The kinetics of ICP8-GFP expression was similar to that of the wildtype ICP8, but the amount of labeled ICP8-GFP protein was partially decreased. Thus, the recombinant ICP8-GFP virus expresses only the fusion protein and neither the wildtype ICP8 nor the parental ICP8-lacZ proteins.

To determine if the virus could grow in normal cells, single-cycle growth experiments were performed in both an ICP8 complementing cell line (S2) and a noncomplementing cell line (Vero). Monolayers of cells were infected at an moi of 3 or 20 and virus was harvested 24 hours post-infection as described above. The resulting virus was titered on S2 cells. The 8GFP viral yields at an moi 20 were $6.6 \times 10^7$ pfu/ml and $4.6 \times 10^5$ pfu/ml on the S2 and Vero cells, respectively (see FIG. 2). Therefore, the virus can grow on Vero cells, but the yield is increased almost 150 fold by growing the virus on an ICP8-GFP complementing cell line. Thus, the virus appears to be compromised in Vero cells at some point in the replication cycle. The ICP8-GFP virus can grow to wildtype titers on an ICP8 complementing cell line.

To analyze ICP8-GFP viral DNA synthesis in Vero cells, viral DNA replication assays were performed. Vero cell monolayers in T25 flasks were infected with either KOS 1.1 or the ICP8-GFP virus at an moi of 3 or 10 in the presence or absence of the specific viral DNA inhibitor phosphonoacetic acid (PAA) (400 µg/ml). At 16 hours post-infection, total DNA was obtained by lysing the cells in 3 ml lysis buffer (10 mM Tris-Cl, pH 8.0, 10 mM EDTA, pH 8.0, 2% SDS, 100 µg/ml proteinase K) and incubated overnight at 37° C. After the addition of 0.3 ml 3M sodium acetate (pH5.2), lysates were extracted once with phenol:chloroform and then once with chloroform. After precipitation with 2 volumes 70% ethanol and resuspension in 700 µl TE, the lysate was digested RNase A (25 µg/ml) for 30 minutes at 37° C. 70 µl of 3M sodium acetate (pH5.2) was added and then the samples were once again extracted with phenol:chloroform and then once with chloroform. The DNA was precipitated on ice for one hour by the addition of an equal volume of 1.6 M NaCl-13% PEG. The DNA was then resuspended in TE quantitated. Equivalent amounts of DNA were applied to a nitrocellulose filter in five fold dilutions (2000 ng–16 ng in 12×SSC) via a dot-blotter apparatus. The filter was then probed with HSV-1 specific $^{32}$P-labeled plasmid pSV8.3. Exposure and quantification of the filter was with the BioRad GS-525 Molecular Imager and Multi-Analyst software. The values were corrected for the amount of input viral DNA, as measured by the signal from lanes containing PAA. At an moi 3, ICP8-GFP viral DNA synthesis was decreased 33-fold compared to KOS 1.1 infection. The defect was slightly diminished at an moi of 10 with a decrease in viral DNA synthesis of 20-fold compared to KOS 1.1. Therefore, the partial block in viral replication in Vero cells may be at the level of viral DNA synthesis.

Figure 3A:
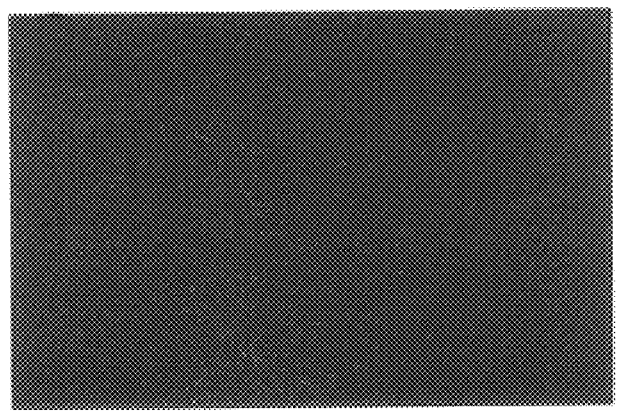
FIGS. 3A, 3B and 3C illustrate the localization of 8GFP in cultured S2 cells.
Figure 3B:
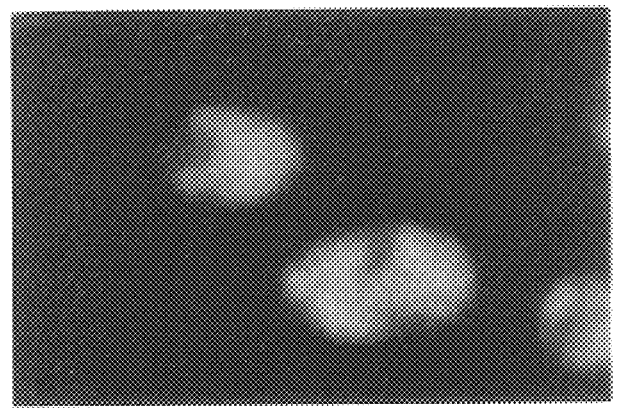
Figure 3C:
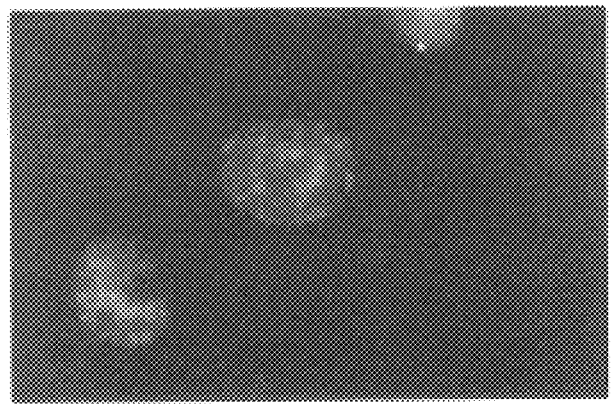

To analyze replication compartment formation, Vero or S2 cells grown on 22×22 mm coverslips were infected at an moi of 20 with either the ICP8-GFP virus or KOS 1.1 as a control. At various times post-infection, cells were fixed for 3 minutes in 3.7% formaldehyde in PBS, and then the coverslips were mounted on slides with glycerol:gelatin. The ICP8-GFP fusion protein was visualized using a filter set designed to detect FITC staining. By 4–4.5 hours post-infection all cells had glowing nuclei with small replication compartments observed in most Vero or S2 cells infected with the ICP8-GFP virus. At no time was glowing observed in either mock or KOS 1.1 infected Vero or S2 cells. At 6 to 9 hours post-infection, the replication compartments increased in size, but in Vero cells the replication compartments did not grow as large as the compartments observed in the infected S2 cells. Thus, the kinetics of replication compartment formation in ICP8-GFP infection was similar to wildtype infection, but the size of the compartments in Vero cells was smaller than what was observed in the infected ICP8 complementing S2 cells. Replication compartments were also observed in cultured Vero or S2 cells with the use of an inverted, fluorescent Nikon Microscope (see FIG. 3). It appears as though the ICP8-GFP fusion protein is targeted to the proper intranuclear regions, but it is compromised for a function that is required for the development of large replication compartments. Therefore, the fusion protein appears to be partially deficient in an activity that is required after correct intranuclear localization, but prior to viral DNA synthesis. This deficiency apparently can be complemented by the presence of the wildtype ICP8 protein since the S2 cells, replication compartment formation was near wildtype in both kinetics and size.

Figure 4A:
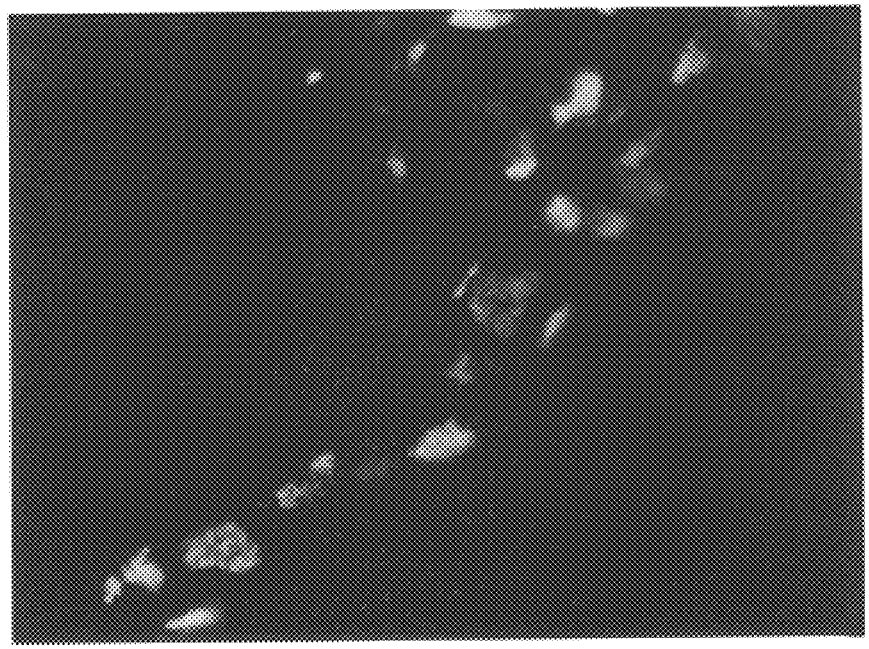
FIGS. 4A and 4B demonstrate the expression of 8GFP in murine cornea at two days post-infection.
Figure 4B:
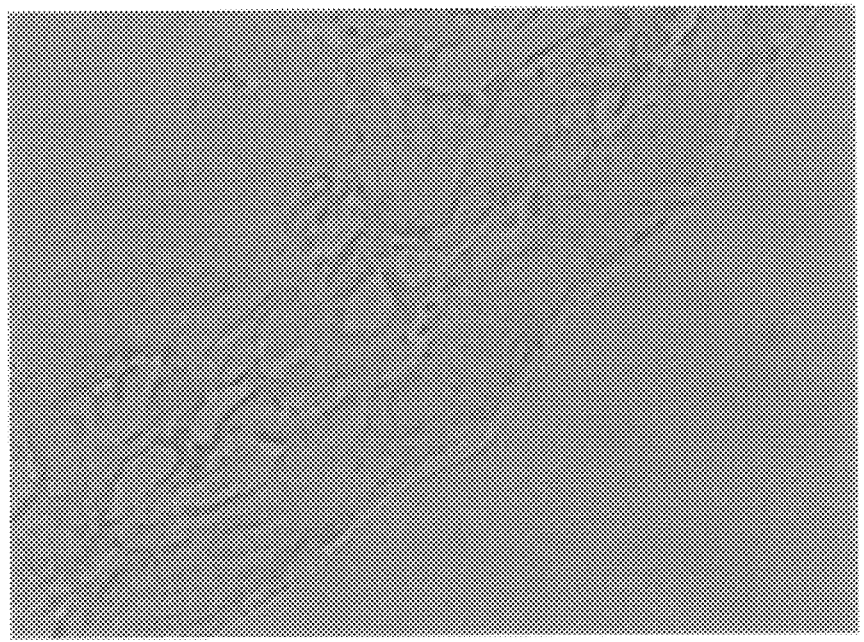
Figure 5A:
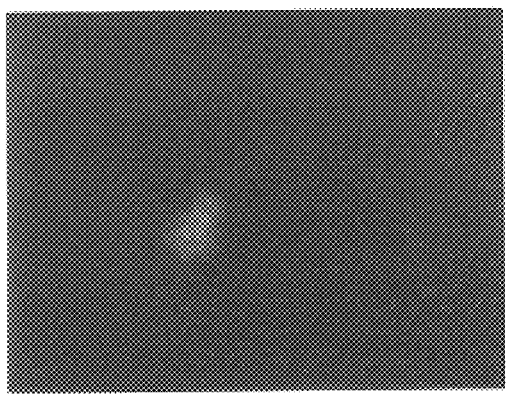
FIGS. 5A–5D show the expression of 8GFP in murine trigeminal ganglia neurons at four days post-infection.
Figure 5B:
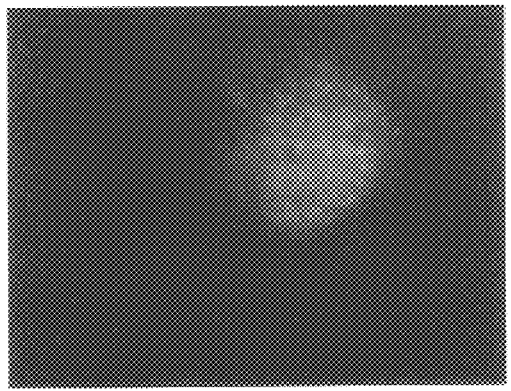
Figure 5C:
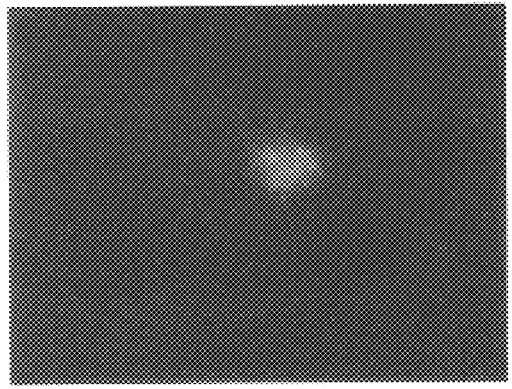
Figure 5D:
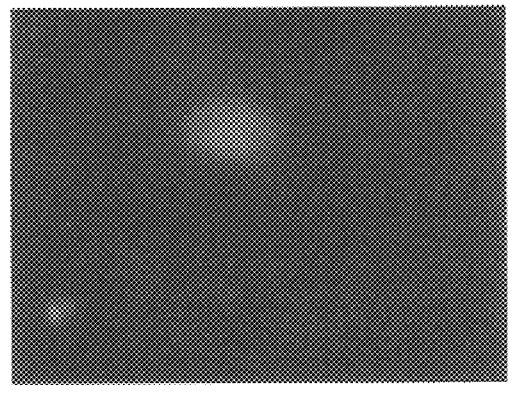

To determine if the recombinant 8GFP virus could be used to observe infected cells in vivo, mice were co-infected via corneal scarification with 8GFP and KOS 1.1 at $2 \times 10^6$ PFU/eye each. At 2 and 4 days post injection, eyes and trigeminal ganglia were removed, respectively, and processed for visualization of 8GFP by cryo-sectioning. In both corneal and ganglion sections, infected cells could be observed (see FIGS. 4 and 5). Thus, the 8GFP virus may be used to study the in vivo localization of ICP8 or simply to identify HSV-1 infected cells in vivo.

While this invention has been particularly shown and described with references to preferred embodiments thereof, it will be understood by those skilled in the art that various changes in form and details may be made therein without departing from the spirit and scope of the invention as defined by the appended claims.

SEQUENCE LISTING

<160> NUMBER OF SEQ ID NOS: 6

<210> SEQ ID NO 1
<211> LENGTH: 4359
<212> TYPE: DNA
<213> ORGANISM: herpesvirus
<220> FEATURE:
<221> NAME/KEY: CDS
<222> LOCATION: (1)...(4359)

<400> SEQUENCE: 1

```
atg gag aca aag ccc aag acg gca acc acc atc aag gtc ccc ccc ggg      48
Met Glu Thr Lys Pro Lys Thr Ala Thr Thr Ile Lys Val Pro Pro Gly
 1               5                  10                  15 ccc ctg gga tac gtg tac gct cgc gcg tgt ccg tcc gaa ggc atc gag      96
Pro Leu Gly Tyr Val Tyr Ala Arg Ala Cys Pro Ser Glu Gly Ile Glu
             20                  25                  30 ctt ctg gcg tta ctg tcg gcg cgc agc ggc gat gcc gac gtc gcc gtg     144
Leu Leu Ala Leu Leu Ser Ala Arg Ser Gly Asp Ala Asp Val Ala Val
         35                  40                  45 gcg ccc ctg gtc gtg ggc ctg acc gtg gag agc ggc ttt gag gcc aac     192
Ala Pro Leu Val Val Gly Leu Thr Val Glu Ser Gly Phe Glu Ala Asn
     50                  55                  60 gta gcc gtg gtc gtg ggt tct cgc acg acg ggg ctc ggg ggt acc gcg     240
Val Ala Val Val Val Gly Ser Arg Thr Thr Gly Leu Gly Gly Thr Ala
 65                  70                  75                  80 gtg tcc ctg aaa ctg acg cca tcg cac tac agc tcg tcc gtg tac gtc     288
Val Ser Leu Lys Leu Thr Pro Ser His Tyr Ser Ser Ser Val Tyr Val
                 85                  90                  95 ttt cac ggc ggc cgg cac ctg gac ccc agc acc cag gcc cca aac ctg     336
Phe His Gly Gly Arg His Leu Asp Pro Ser Thr Gln Ala Pro Asn Leu
            100                 105                 110 acg cga ctc tgc gag cgg gca cgc cgc cat ttt ggc ttt tcg gac tac     384
Thr Arg Leu Cys Glu Arg Ala Arg Arg His Phe Gly Phe Ser Asp Tyr
        115                 120                 125 acc ccc cgg ccc ggc gac ctc aaa cac gag acg acg ggg gag gcg ctg     432
Thr Pro Arg Pro Gly Asp Leu Lys His Glu Thr Thr Gly Glu Ala Leu
    130                 135                 140 tgt gag cgc ctc ggc ctg gac ccg gac cgc gcc ctc ctg tat ctg gtc     480
Cys Glu Arg Leu Gly Leu Asp Pro Asp Arg Ala Leu Leu Tyr Leu Val
145                 150                 155                 160 gtt acc gag ggc ttc aag gag gcc gtg tgc atc aac aac acc ttt ctg     528
Val Thr Glu Gly Phe Lys Glu Ala Val Cys Ile Asn Asn Thr Phe Leu
                165                 170                 175 cac ctg gga ggc tcg gac aag gta acc ata ggc ggg gcg gag gtg cac     576
His Leu Gly Gly Ser Asp Lys Val Thr Ile Gly Gly Ala Glu Val His
            180                 185                 190 cgc ata ccc gtg tat ccg ttg cag ctg ttc atg ccg gat ttt agc cgg     624
Arg Ile Pro Val Tyr Pro Leu Gln Leu Phe Met Pro Asp Phe Ser Arg
```

|  |  |  |  |  |  |  |  |  |  |  |  |  |  |  |  |
|---|---|---|---|---|---|---|---|---|---|---|---|---|---|---|---|
|  |  | 195 |  |  |  |  | 200 |  |  |  |  | 205 |  |  |  |

```
gtc atc gcc gag ccg ttc aac gcc aac cac cga tcg atc ggg gag aat    672
Val Ile Ala Glu Pro Phe Asn Ala Asn His Arg Ser Ile Gly Glu Asn
    210                 215                 220 ttt acc tac ccg ctt ccg ttt ttt aac cgc ccc ctc aac cgc ctc ctg    720
Phe Thr Tyr Pro Leu Pro Phe Phe Asn Arg Pro Leu Asn Arg Leu Leu
225                 230                 235                 240 ttc gag gcg gtc gtg gga ccc gcc gcc gtg gca ctg cga tgc cga aac    768
Phe Glu Ala Val Val Gly Pro Ala Ala Val Ala Leu Arg Cys Arg Asn
                245                 250                 255 gtg gac gcc gtg gcc cgc gcg gcc gcc cac ctg gcg ttt gac gaa aac    816
Val Asp Ala Val Ala Arg Ala Ala Ala His Leu Ala Phe Asp Glu Asn
            260                 265                 270 cac gag ggc gcc gcc ctc ccc gcc gac att acg ttc acg gcc ttc gaa    864
His Glu Gly Ala Ala Leu Pro Ala Asp Ile Thr Phe Thr Ala Phe Glu
        275                 280                 285 gcc agc cag ggt aag acc ccg cgg ggt ggg cgc gac ggc ggc ggc aag    912
Ala Ser Gln Gly Lys Thr Pro Arg Gly Gly Arg Asp Gly Gly Gly Lys
    290                 295                 300 ggc ccg gcg ggc ggg ttc gaa cag cgc ctg gcc tcc gtc atg gcc gga    960
Gly Pro Ala Gly Gly Phe Glu Gln Arg Leu Ala Ser Val Met Ala Gly
305                 310                 315                 320 gac gcc gcc ctg gcc ctc gag tct atc gtg tcg atg gcc gtc ttc gac   1008
Asp Ala Ala Leu Ala Leu Glu Ser Ile Val Ser Met Ala Val Phe Asp
                325                 330                 335 gag ccg ccc acc gac atc tcc gcg tgg ccg ctg tgc gag ggc cag gac   1056
Glu Pro Pro Thr Asp Ile Ser Ala Trp Pro Leu Cys Glu Gly Gln Asp
            340                 345                 350 acg gcc gcg gcc cgc gcc aac gcc gtc ggg gcg tac ctg gcg cgc gcc   1104
Thr Ala Ala Ala Arg Ala Asn Ala Val Gly Ala Tyr Leu Ala Arg Ala
        355                 360                 365 gcg gga ctc gtg ggg gcc atg gta ttt agc acc aac tcg gcc ctc cat   1152
Ala Gly Leu Val Gly Ala Met Val Phe Ser Thr Asn Ser Ala Leu His
    370                 375                 380 ctc acc gag gtg gac gac gcc ggt ccg gcg gac cca aag gac cac agc   1200
Leu Thr Glu Val Asp Asp Ala Gly Pro Ala Asp Pro Lys Asp His Ser
385                 390                 395                 400 aaa ccc tcc ttt tac cgc ttc ttc ctc gtg ccc ggg acc cac gtg gcg   1248
Lys Pro Ser Phe Tyr Arg Phe Phe Leu Val Pro Gly Thr His Val Ala
                405                 410                 415 gcc aac cca cag gtg gac cgc gag gga cac gtg gtg ccc ggg ttc gag   1296
Ala Asn Pro Gln Val Asp Arg Glu Gly His Val Val Pro Gly Phe Glu
            420                 425                 430 ggt cgg ccc acc gcg ccc ctc gtc ggc gga acc cag gaa ttt gcc ggc   1344
Gly Arg Pro Thr Ala Pro Leu Val Gly Gly Thr Gln Glu Phe Ala Gly
        435                 440                 445 gag cac ctg gcc atg ctg tgt ggg ttt tcc ccg gcg ctg ctg gcc aag   1392
Glu His Leu Ala Met Leu Cys Gly Phe Ser Pro Ala Leu Leu Ala Lys
    450                 455                 460 atg ctg ttt tac ctg gag cgc tgc gac ggc ggc gtg atc gtc ggg cgc   1440
Met Leu Phe Tyr Leu Glu Arg Cys Asp Gly Gly Val Ile Val Gly Arg
465                 470                 475                 480 cag gag atg gac gtg ttt cga tac gtc gcg gac tcc aac cag acc gac   1488
Gln Glu Met Asp Val Phe Arg Tyr Val Ala Asp Ser Asn Gln Thr Asp
                485                 490                 495 gtg ccc tgc aac ctg tgc acc ttc gac acg cgc cac gcc tgc gta cac   1536
Val Pro Cys Asn Leu Cys Thr Phe Asp Thr Arg His Ala Cys Val His
            500                 505                 510 acg acg ctc atg cgc ctc cgg gcg cgc cat ccc aag ttc gcc agc gcc   1584
```

```
                                                                -continued

Thr Thr Leu Met Arg Leu Arg Ala Arg His Pro Lys Phe Ala Ser Ala
            515                 520                 525 gcc cgc gga gcc atc ggc gtc ttc ggg acc atg aac agc atg tac agc        1632
Ala Arg Gly Ala Ile Gly Val Phe Gly Thr Met Asn Ser Met Tyr Ser
        530                 535                 540 gac tgc gac gtg ctg gga aac tac gcc gcc ttc tcg gcc ctg aag cgc        1680
Asp Cys Asp Val Leu Gly Asn Tyr Ala Ala Phe Ser Ala Leu Lys Arg
545                 550                 555                 560 gcg gac gga tcc gag acc gcc cgg acc atc atg cag gag acg tac cgc        1728
Ala Asp Gly Ser Glu Thr Ala Arg Thr Ile Met Gln Glu Thr Tyr Arg
                565                 570                 575 gcg gcg acc gag cgc gtc atg gcc gaa ctc gag acc ctg cag tac gtg        1776
Ala Ala Thr Glu Arg Val Met Ala Glu Leu Glu Thr Leu Gln Tyr Val
            580                 585                 590 gac cag gcg gtc ccc acg gcc atg ggg cgg ctg gag acc atc atc acc        1824
Asp Gln Ala Val Pro Thr Ala Met Gly Arg Leu Glu Thr Ile Ile Thr
        595                 600                 605 aac cgc gag gcc ctg cat acg gtg gtg aac aac gtc agg cag gtc gtg        1872
Asn Arg Glu Ala Leu His Thr Val Val Asn Asn Val Arg Gln Val Val
    610                 615                 620 gac cgc gag gtg gag cag ctg atg cgc aac ctg gtg gag ggg agg aac        1920
Asp Arg Glu Val Glu Gln Leu Met Arg Asn Leu Val Glu Gly Arg Asn
625                 630                 635                 640 ttc aag ttt cgc gac ggt ctg ggc gag gcc aac cac gcc atg tcc ctg        1968
Phe Lys Phe Arg Asp Gly Leu Gly Glu Ala Asn His Ala Met Ser Leu
                645                 650                 655 acg ctg gac ccg tac gcg tgc ggg cca tgc ccc ctg ctt cag ctt ctc        2016
Thr Leu Asp Pro Tyr Ala Cys Gly Pro Cys Pro Leu Leu Gln Leu Leu
            660                 665                 670 ggg cgg cga tcc aac ctc gcc gtg tat cag gac ctg gcc ctg agc cag        2064
Gly Arg Arg Ser Asn Leu Ala Val Tyr Gln Asp Leu Ala Leu Ser Gln
        675                 680                 685 tgc cac ggg gtg ttc gcc ggg cag tcg gtc gag ggg cgc aac ttt cgc        2112
Cys His Gly Val Phe Ala Gly Gln Ser Val Glu Gly Arg Asn Phe Arg
    690                 695                 700 aat caa ttc caa ccg gtg ctg cgg cgg cgc gtg atg gac atg ttt aac        2160
Asn Gln Phe Gln Pro Val Leu Arg Arg Arg Val Met Asp Met Phe Asn
705                 710                 715                 720 aac ggg ttt ctg tcg gcc aaa acg ctg acg gtc gcg ctc tcg gag ggg        2208
Asn Gly Phe Leu Ser Ala Lys Thr Leu Thr Val Ala Leu Ser Glu Gly
                725                 730                 735 gcg gct atc tgc gcc ccc agc cta acg gcc ggc cag acg gcc ccc gcc        2256
Ala Ala Ile Cys Ala Pro Ser Leu Thr Ala Gly Gln Thr Ala Pro Ala
            740                 745                 750 gag agc agc ttc gag ggc gac gtt gcc cgc gtg acc ctg ggg ttt ccc        2304
Glu Ser Ser Phe Glu Gly Asp Val Ala Arg Val Thr Leu Gly Phe Pro
        755                 760                 765 aag gag ctg cgc gtc aag agc cgc gtg ttg ttc gcg ggc gcg agc gcc        2352
Lys Glu Leu Arg Val Lys Ser Arg Val Leu Phe Ala Gly Ala Ser Ala
    770                 775                 780 aac gcg tcc gag gcc gcc aag gcg cgg gtc gcc agc ctc cag agc gcc        2400
Asn Ala Ser Glu Ala Ala Lys Ala Arg Val Ala Ser Leu Gln Ser Ala
785                 790                 795                 800 tac cag aag ccc gac aag cgc gtg gac atc ctc ctc gga ccg ctg ggc        2448
Tyr Gln Lys Pro Asp Lys Arg Val Asp Ile Leu Leu Gly Pro Leu Gly
                805                 810                 815 ttt ctg ctg aag cag ttc cac gcg gcc atc ttc ccc aac ggc aag ccc        2496
Phe Leu Leu Lys Gln Phe His Ala Ala Ile Phe Pro Asn Gly Lys Pro
            820                 825                 830
```

```
ccg ggg tcc aac cag ccg aac ccg cag tgg ttc tgg acg gcc ctc caa          2544
Pro Gly Ser Asn Gln Pro Asn Pro Gln Trp Phe Trp Thr Ala Leu Gln
            835                 840                 845 cgc aac cag ctt ccc gcc cgg ctc ctg tcg cgc gag gac atc gag acc          2592
Arg Asn Gln Leu Pro Ala Arg Leu Leu Ser Arg Glu Asp Ile Glu Thr
850                 855                 860 atc gcg ttc att aaa aag ttt tcc ctg gac tac ggc gcg ata aac ttt          2640
Ile Ala Phe Ile Lys Lys Phe Ser Leu Asp Tyr Gly Ala Ile Asn Phe
865                 870                 875                 880 att aac ctg gcc ccc aac aac gtg agc gag ctg gcg atg tac tac atg          2688
Ile Asn Leu Ala Pro Asn Asn Val Ser Glu Leu Ala Met Tyr Tyr Met
            885                 890                 895 gca aac cag att ctg cgg tac tgc gat cac tcg aca tac ttc atc aac          2736
Ala Asn Gln Ile Leu Arg Tyr Cys Asp His Ser Thr Tyr Phe Ile Asn
900                 905                 910 acc ctc acg gcc atc atc gcg ggg tcc cgc cgt ccc ccc agc gtg cag          2784
Thr Leu Thr Ala Ile Ile Ala Gly Ser Arg Arg Pro Pro Ser Val Gln
915                 920                 925 gcg gcg gcc gcg tgg tcc gcg cag ggc ggg gcg ggc ctg gag gcc ggg          2832
Ala Ala Ala Ala Trp Ser Ala Gln Gly Gly Ala Gly Leu Glu Ala Gly
930                 935                 940 gcc cgc gcg ctg atg gac gcc gtg gac gcg cat ccg ggc gcg tgg acg          2880
Ala Arg Ala Leu Met Asp Ala Val Asp Ala His Pro Gly Ala Trp Thr
945                 950                 955                 960 tcc atg ttc gcc agc tgc aac ctg ctg cgg ccc gtc atg gcg gcg cgc          2928
Ser Met Phe Ala Ser Cys Asn Leu Leu Arg Pro Val Met Ala Ala Arg
            965                 970                 975 ccc atg gtc gtg ttg ggg ttg agc atc agc aaa tac tac ggc atg gcc          2976
Pro Met Val Val Leu Gly Leu Ser Ile Ser Lys Tyr Tyr Gly Met Ala
            980                 985                 990 ggc aac gac cgt gtg ttt cag gcc ggg aac tgg gcc agc ctg atg ggc          3024
Gly Asn Asp Arg Val Phe Gln Ala Gly Asn Trp Ala Ser Leu Met Gly
            995                 1000                1005 ggc aaa aac gcg tgc ccg ctc ctt att ttt gac cgc acc cgc aag ttc          3072
Gly Lys Asn Ala Cys Pro Leu Leu Ile Phe Asp Arg Thr Arg Lys Phe
        1010                1015                1020 gtc ctg gcc tgt ccc cgg gcc ggg ttt gtg tgc gcg gcc tcg aac ctc          3120
Val Leu Ala Cys Pro Arg Ala Gly Phe Val Cys Ala Ala Ser Asn Leu
1025                1030                1035                1040 ggc ggc gga gcg cac gaa agc tcg ctg tgc gag cag ctc cgg ggc att          3168
Gly Gly Gly Ala His Glu Ser Ser Leu Cys Glu Gln Leu Arg Gly Ile
                1045                1050                1055 atc tcc gag ggc ggg gcg gcc gtc gcc agt agc gtg ttc gtg gcg acc          3216
Ile Ser Glu Gly Gly Ala Ala Val Ala Ser Ser Val Phe Val Ala Thr
                1060                1065                1070 gtg aaa agc ctg ggg ccc cgc acc cag cag ctg cag atc gag gac tgg          3264
Val Lys Ser Leu Gly Pro Arg Thr Gln Gln Leu Gln Ile Glu Asp Trp
            1075                1080                1085 ctg gcg ctc ctg gag gac gag tac cta agc gag gag atg atg gag ctg          3312
Leu Ala Leu Leu Glu Asp Glu Tyr Leu Ser Glu Glu Met Met Glu Leu
1090                1095                1100 acc gcg cgt gcc ctg gag cgc ggc aac ggc gag tgg tcg acg gac gcg          3360
Thr Ala Arg Ala Leu Glu Arg Gly Asn Gly Glu Trp Ser Thr Asp Ala
1105                1110                1115                1120 gcc ctg gag gtg gcg cac gag gcc gag gcc cta gtc agc caa ctc ggc          3408
Ala Leu Glu Val Ala His Glu Ala Glu Ala Leu Val Ser Gln Leu Gly
                1125                1130                1135 aac gcc ggg gag gtg ttt aac ttt ggg gat ttt ggc tgc gag gac gac          3456
Asn Ala Gly Glu Val Phe Asn Phe Gly Asp Phe Gly Cys Glu Asp Asp
            1140                1145                1150
```

```
aac gcg acg ccg ttc ggc ggc ccg ggg gcc ccg gga ccg gca ttt gcc    3504
Asn Ala Thr Pro Phe Gly Gly Pro Gly Ala Pro Gly Pro Ala Phe Ala
            1155                1160                1165 ggc cgc aaa cgg gcg ttc cac ggg gat gac ccg ttt ggg gag ggg ccc    3552
Gly Arg Lys Arg Ala Phe His Gly Asp Asp Pro Phe Gly Glu Gly Pro
    1170                1175                1180 ccc gac aaa aag gga gac ctg acg ttg gat atg ctg aga ggg gtt ggg    3600
Pro Asp Lys Lys Gly Asp Leu Thr Leu Asp Met Leu Arg Gly Val Gly
1185                1190                1195                1200 ggg tgg ggg aac cta gag tcg acc cgg gcg gcc gcc gcc acc atg agc    3648
Gly Trp Gly Asn Leu Glu Ser Thr Arg Ala Ala Ala Ala Thr Met Ser
                1205                1210                1215 aag ggc gag gaa ctg ttc act ggc gtg gtc cca att ctc gtg gaa ctg    3696
Lys Gly Glu Glu Leu Phe Thr Gly Val Val Pro Ile Leu Val Glu Leu
            1220                1225                1230 gat ggc gat gtg aat ggg cac aaa ttt tct gtc agc gga gag ggt gaa    3744
Asp Gly Asp Val Asn Gly His Lys Phe Ser Val Ser Gly Glu Gly Glu
        1235                1240                1245 ggt gat gcc aca tac gga aag ctc acc ctg aaa ttc atc tgc acc act    3792
Gly Asp Ala Thr Tyr Gly Lys Leu Thr Leu Lys Phe Ile Cys Thr Thr
    1250                1255                1260 gga aag ctc cct gtg cca tgg cca aca ctg gtc act acc ttc acc tat    3840
Gly Lys Leu Pro Val Pro Trp Pro Thr Leu Val Thr Thr Phe Thr Tyr
1265                1270                1275                1280 ggc gtg cag tgc ttt tcc aga tac cca gac cat atg aag cag cat gac    3888
Gly Val Gln Cys Phe Ser Arg Tyr Pro Asp His Met Lys Gln His Asp
                1285                1290                1295 ttt ttc aag agc gcc atg ccc gag ggc tat gtg cag gag aga acc atc    3936
Phe Phe Lys Ser Ala Met Pro Glu Gly Tyr Val Gln Glu Arg Thr Ile
            1300                1305                1310 ttt ttc aaa gat gac ggg aac tac aag acc cgc gct gaa gtc aag ttc    3984
Phe Phe Lys Asp Asp Gly Asn Tyr Lys Thr Arg Ala Glu Val Lys Phe
        1315                1320                1325 gaa ggt gac acc ctg gtg aat aga atc gag ttg aag ggc att gac ttt    4032
Glu Gly Asp Thr Leu Val Asn Arg Ile Glu Leu Lys Gly Ile Asp Phe
    1330                1335                1340 aag gaa gat gga aac att ctc ggc cac aag ctg gaa tac aac tat aac    4080
Lys Glu Asp Gly Asn Ile Leu Gly His Lys Leu Glu Tyr Asn Tyr Asn
1345                1350                1355                1360 tcc cac aat gtg tac atc atg gcc gac aag caa aag aat ggc atc aag    4128
Ser His Asn Val Tyr Ile Met Ala Asp Lys Gln Lys Asn Gly Ile Lys
                1365                1370                1375 gtc aac ttc aag atc aga cac aac att gag gat gga tcc gtg cag ctg    4176
Val Asn Phe Lys Ile Arg His Asn Ile Glu Asp Gly Ser Val Gln Leu
            1380                1385                1390 gcc gac cat tat caa cag aac act cca atc ggc gac ggc cct gtg ctc    4224
Ala Asp His Tyr Gln Gln Asn Thr Pro Ile Gly Asp Gly Pro Val Leu
        1395                1400                1405 ctc cca gac aac cat tac ctg tcc acc cag tct gcc ctg tct aaa gat    4272
Leu Pro Asp Asn His Tyr Leu Ser Thr Gln Ser Ala Leu Ser Lys Asp
    1410                1415                1420 ccc aac gaa aag aga gac cac atg gtc ctg ctg gag ttt gtg acc gct    4320
Pro Asn Glu Lys Arg Asp His Met Val Leu Leu Glu Phe Val Thr Ala
1425                1430                1435                1440 gct ggg atc aca cat ggc atg gac gag ctg tac aag tga              4359
Ala Gly Ile Thr His Gly Met Asp Glu Leu Tyr Lys
                1445                1450

<210> SEQ ID NO 2
```

-continued

```
<211> LENGTH: 1452
<212> TYPE: PRT
<213> ORGANISM: herpesvirus

<400> SEQUENCE: 2

Met Glu Thr Lys Pro Lys Thr Ala Thr Thr Ile Lys Val Pro Pro Gly
 1               5                  10                  15

Pro Leu Gly Tyr Val Tyr Ala Arg Ala Cys Pro Ser Glu Gly Ile Glu
            20                  25                  30

Leu Leu Ala Leu Leu Ser Ala Arg Ser Gly Asp Ala Asp Val Ala Val
        35                  40                  45

Ala Pro Leu Val Val Gly Leu Thr Val Glu Ser Gly Phe Glu Ala Asn
    50                  55                  60

Val Ala Val Val Val Gly Ser Arg Thr Thr Gly Leu Gly Gly Thr Ala
65                  70                  75                  80

Val Ser Leu Lys Leu Thr Pro Ser His Tyr Ser Ser Val Tyr Val
                85                  90                  95

Phe His Gly Gly Arg His Leu Asp Pro Ser Thr Gln Ala Pro Asn Leu
            100                 105                 110

Thr Arg Leu Cys Glu Arg Ala Arg Arg His Phe Gly Phe Ser Asp Tyr
        115                 120                 125

Thr Pro Arg Pro Gly Asp Leu Lys His Glu Thr Thr Gly Glu Ala Leu
    130                 135                 140

Cys Glu Arg Leu Gly Leu Asp Pro Asp Arg Ala Leu Leu Tyr Leu Val
145                 150                 155                 160

Val Thr Glu Gly Phe Lys Glu Ala Val Cys Ile Asn Asn Thr Phe Leu
                165                 170                 175

His Leu Gly Gly Ser Asp Lys Val Thr Ile Gly Gly Ala Glu Val His
            180                 185                 190

Arg Ile Pro Val Tyr Pro Leu Gln Leu Phe Met Pro Asp Phe Ser Arg
        195                 200                 205

Val Ile Ala Glu Pro Phe Asn Ala Asn His Arg Ser Ile Gly Glu Asn
    210                 215                 220

Phe Thr Tyr Pro Leu Pro Phe Phe Asn Arg Pro Leu Asn Arg Leu Leu
225                 230                 235                 240

Phe Glu Ala Val Val Gly Pro Ala Val Ala Leu Arg Cys Arg Asn
                245                 250                 255

Val Asp Ala Val Ala Arg Ala Ala His Leu Ala Phe Asp Glu Asn
            260                 265                 270

His Glu Gly Ala Ala Leu Pro Ala Asp Ile Thr Phe Thr Ala Phe Glu
        275                 280                 285

Ala Ser Gln Gly Lys Thr Pro Arg Gly Gly Arg Asp Gly Gly Lys
    290                 295                 300

Gly Pro Ala Gly Gly Phe Glu Gln Arg Leu Ala Ser Val Met Ala Gly
305                 310                 315                 320

Asp Ala Ala Leu Ala Leu Glu Ser Ile Val Ser Met Ala Val Phe Asp
                325                 330                 335

Glu Pro Pro Thr Asp Ile Ser Ala Trp Pro Leu Cys Glu Gly Gln Asp
            340                 345                 350

Thr Ala Ala Arg Ala Asn Ala Val Gly Ala Tyr Leu Ala Arg Ala
        355                 360                 365

Ala Gly Leu Val Gly Ala Met Val Phe Ser Thr Asn Ser Ala Leu His
    370                 375                 380

Leu Thr Glu Val Asp Asp Ala Gly Pro Ala Asp Pro Lys Asp His Ser
```

-continued

```
385                 390                 395                 400

Lys Pro Ser Phe Tyr Arg Phe Leu Val Pro Gly Thr His Val Ala
                405                 410             415

Ala Asn Pro Gln Val Asp Arg Glu Gly His Val Pro Gly Phe Glu
            420                 425             430

Gly Arg Pro Thr Ala Pro Leu Val Gly Thr Gln Glu Phe Ala Gly
            435                 440             445

Glu His Leu Ala Met Leu Cys Gly Phe Ser Pro Ala Leu Leu Ala Lys
        450                 455             460

Met Leu Phe Tyr Leu Glu Arg Cys Asp Gly Val Ile Val Gly Arg
465                 470                 475                 480

Gln Glu Met Asp Val Phe Arg Tyr Val Ala Asp Ser Asn Gln Thr Asp
                485                 490                 495

Val Pro Cys Asn Leu Cys Thr Phe Asp Thr Arg His Ala Cys Val His
                500                 505             510

Thr Thr Leu Met Arg Leu Arg Ala Arg His Pro Lys Phe Ala Ser Ala
            515                 520             525

Ala Arg Gly Ala Ile Gly Val Phe Gly Thr Met Asn Ser Met Tyr Ser
        530                 535                 540

Asp Cys Asp Val Leu Gly Asn Tyr Ala Ala Phe Ser Ala Leu Lys Arg
545                 550                 555                 560

Ala Asp Gly Ser Glu Thr Ala Arg Thr Ile Met Gln Glu Thr Tyr Arg
                565                 570                 575

Ala Ala Thr Glu Arg Val Met Ala Glu Leu Glu Thr Leu Gln Tyr Val
            580                 585             590

Asp Gln Ala Val Pro Thr Ala Met Gly Arg Leu Glu Thr Ile Ile Thr
        595                 600                 605

Asn Arg Glu Ala Leu His Thr Val Val Asn Asn Val Arg Gln Val Val
    610                 615                 620

Asp Arg Glu Val Glu Gln Leu Met Arg Asn Leu Val Glu Gly Arg Asn
625                 630                 635                 640

Phe Lys Phe Arg Asp Gly Leu Gly Glu Ala Asn His Ala Met Ser Leu
                645                 650                 655

Thr Leu Asp Pro Tyr Ala Cys Gly Pro Cys Pro Leu Leu Gln Leu Leu
            660                 665             670

Gly Arg Arg Ser Asn Leu Ala Val Tyr Gln Asp Leu Ala Leu Ser Gln
            675                 680             685

Cys His Gly Val Phe Ala Gly Gln Ser Val Glu Gly Arg Asn Phe Arg
        690                 695             700

Asn Gln Phe Gln Pro Val Leu Arg Arg Val Met Asp Met Phe Asn
705                 710                 715             720

Asn Gly Phe Leu Ser Ala Lys Thr Leu Thr Val Ala Leu Ser Glu Gly
            725                 730                 735

Ala Ala Ile Cys Ala Pro Ser Leu Thr Ala Gly Gln Thr Ala Pro Ala
            740                 745             750

Glu Ser Ser Phe Glu Gly Asp Val Ala Arg Val Thr Leu Gly Phe Pro
    755                 760                 765

Lys Glu Leu Arg Val Lys Ser Arg Val Leu Phe Ala Gly Ala Ser Ala
    770                 775                 780

Asn Ala Ser Glu Ala Ala Lys Ala Arg Val Ala Ser Leu Gln Ser Ala
785                 790                 795                 800

Tyr Gln Lys Pro Asp Lys Arg Val Asp Ile Leu Leu Gly Pro Leu Gly
                805                 810             815
```

-continued

```
Phe Leu Leu Lys Gln Phe His Ala Ala Ile Phe Pro Asn Gly Lys Pro
            820                 825                 830
Pro Gly Ser Asn Gln Pro Asn Pro Gln Trp Phe Trp Thr Ala Leu Gln
        835                 840                 845
Arg Asn Gln Leu Pro Ala Arg Leu Leu Ser Arg Glu Asp Ile Glu Thr
    850                 855                 860
Ile Ala Phe Ile Lys Lys Phe Ser Leu Asp Tyr Gly Ala Ile Asn Phe
865                 870                 875                 880
Ile Asn Leu Ala Pro Asn Asn Val Ser Glu Leu Ala Met Tyr Tyr Met
                885                 890                 895
Ala Asn Gln Ile Leu Arg Tyr Cys Asp His Ser Thr Tyr Phe Ile Asn
            900                 905                 910
Thr Leu Thr Ala Ile Ile Ala Gly Ser Arg Arg Pro Pro Ser Val Gln
        915                 920                 925
Ala Ala Ala Ala Trp Ser Ala Gln Gly Gly Ala Gly Leu Glu Ala Gly
    930                 935                 940
Ala Arg Ala Leu Met Asp Ala Val Asp Ala His Pro Gly Ala Trp Thr
945                 950                 955                 960
Ser Met Phe Ala Ser Cys Asn Leu Leu Arg Pro Val Met Ala Ala Arg
                965                 970                 975
Pro Met Val Val Leu Gly Leu Ser Ile Ser Lys Tyr Tyr Gly Met Ala
            980                 985                 990
Gly Asn Asp Arg Val Phe Gln Ala Gly Asn Trp Ala Ser Leu Met Gly
        995                 1000                1005
Gly Lys Asn Ala Cys Pro Leu Leu Ile Phe Asp Arg Thr Arg Lys Phe
    1010                1015                1020
Val Leu Ala Cys Pro Arg Ala Gly Phe Val Cys Ala Ala Ser Asn Leu
1025                1030                1035                1040
Gly Gly Gly Ala His Glu Ser Ser Leu Cys Glu Gln Leu Arg Gly Ile
                1045                1050                1055
Ile Ser Glu Gly Gly Ala Ala Val Ala Ser Ser Val Phe Val Ala Thr
            1060                1065                1070
Val Lys Ser Leu Gly Pro Arg Thr Gln Gln Leu Gln Ile Glu Asp Trp
        1075                1080                1085
Leu Ala Leu Leu Glu Asp Glu Tyr Leu Ser Glu Glu Met Met Glu Leu
    1090                1095                1100
Thr Ala Arg Ala Leu Glu Arg Gly Asn Gly Glu Trp Ser Thr Asp Ala
1105                1110                1115                1120
Ala Leu Glu Val Ala His Glu Ala Glu Ala Leu Val Ser Gln Leu Gly
                1125                1130                1135
Asn Ala Gly Glu Val Phe Asn Phe Gly Asp Phe Gly Cys Glu Asp Asp
            1140                1145                1150
Asn Ala Thr Pro Phe Gly Gly Pro Gly Ala Pro Gly Pro Ala Phe Ala
        1155                1160                1165
Gly Arg Lys Arg Ala Phe His Gly Asp Pro Phe Gly Glu Gly Pro
    1170                1175                1180
Pro Asp Lys Lys Gly Asp Leu Thr Leu Asp Met Leu Arg Gly Val Gly
1185                1190                1195                1200
Gly Trp Gly Asn Leu Glu Ser Thr Arg Ala Ala Ala Thr Met Ser
                1205                1210                1215
Lys Gly Glu Glu Leu Phe Thr Gly Val Val Pro Ile Leu Val Glu Leu
            1220                1225                1230
```

Asp Gly Asp Val Asn Gly His Lys Phe Ser Val Ser Gly Glu Gly Glu
        1235                1240                1245

Gly Asp Ala Thr Tyr Gly Lys Leu Thr Leu Lys Phe Ile Cys Thr Thr
        1250                1255                1260

Gly Lys Leu Pro Val Pro Trp Pro Thr Leu Val Thr Thr Phe Thr Tyr
1265                1270                1275                1280

Gly Val Gln Cys Phe Ser Arg Tyr Pro Asp His Met Lys Gln His Asp
                1285                1290                1295

Phe Phe Lys Ser Ala Met Pro Glu Gly Tyr Val Gln Glu Arg Thr Ile
                1300                1305                1310

Phe Phe Lys Asp Asp Gly Asn Tyr Lys Thr Arg Ala Glu Val Lys Phe
                1315                1320                1325

Glu Gly Asp Thr Leu Val Asn Arg Ile Glu Leu Lys Gly Ile Asp Phe
        1330                1335                1340

Lys Glu Asp Gly Asn Ile Leu Gly His Lys Leu Glu Tyr Asn Tyr Asn
1345                1350                1355                1360

Ser His Asn Val Tyr Ile Met Ala Asp Lys Gln Lys Asn Gly Ile Lys
                1365                1370                1375

Val Asn Phe Lys Ile Arg His Asn Ile Glu Asp Gly Ser Val Gln Leu
                1380                1385                1390

Ala Asp His Tyr Gln Gln Asn Thr Pro Ile Gly Asp Gly Pro Val Leu
                1395                1400                1405

Leu Pro Asp Asn His Tyr Leu Ser Thr Gln Ser Ala Leu Ser Lys Asp
        1410                1415                1420

Pro Asn Glu Lys Arg Asp His Met Val Leu Leu Glu Phe Val Thr Ala
1425                1430                1435                1440

Ala Gly Ile Thr His Gly Met Asp Glu Leu Tyr Lys
                1445                1450

<210> SEQ ID NO 3
<211> LENGTH: 24
<212> TYPE: DNA
<213> ORGANISM: Artificial Sequence
<220> FEATURE:
<223> OTHER INFORMATION: a sense molecule used tomodify the stop codon

<400> SEQUENCE: 3
caacccctct cagcatatcc aacg                                    24

<210> SEQ ID NO 4
<211> LENGTH: 24
<212> TYPE: DNA
<213> ORGANISM: Artificial Sequence
<220> FEATURE:
<223> OTHER INFORMATION: an anti-sense molecule used to modify the stop
      codon

<400> SEQUENCE: 4
cgttggatat gctgagaggg gttg                                    24

<210> SEQ ID NO 5
<211> LENGTH: 12
<212> TYPE: DNA
<213> ORGANISM: Artificial Sequence
<220> FEATURE:
<223> OTHER INFORMATION: oligonucleotide linker

<400> SEQUENCE: 5
ggaagatctt cc                                                 12

```
<210> SEQ ID NO 6
<211> LENGTH:
<212> TYPE:
<213> ORGANISM:

<400> SEQUENCE: 6

This Sequence is intentionally skipped
```

What is claimed is:

1. A fusion protein comprising:
   a) an ICP8 herpesviral protein, wherein the ICP8 herpes viral protein retains all of the functions essential for replication competence in noncomplementing cells; and
   b) a detectable protein,
      wherein the viral protein and detectable protein are fused to maintain the open reading frame.

2. The fusion protein of claim 1, wherein the ICP8 herpesviral protein is an HSV-1 viral protein.

3. The fusion protein of claim 2 wherein the fluorescent protein is a green fluorescent protein.

4. A fusion protein comprising:
   a) a viral ICP8 protein from a herpesvirus, wherein the viral protein retains all of the functions essential for viral growth in noncomplementing cells; and
   b) a detectable protein,
      wherein the viral protein and detectable protein are fused to maintain the open reading frame.

5. The fusion protein of claim 4, wherein the herpesvirus is a Herpes Simplex Virus.

6. The fusion protein of claim 4, wherein the herpesvirus is selected from the group consisting of: a Herpes Simplex Virus-1, a Herpes Simplex Virus-2, a varicella-zoster virus, a Epstein-Barr Virus, a Cytomegalovirus, a Human Herpesvirus-6, and a Human Herpesvirus-7.

7. The fusion protein of claim 4, wherein the detectable protein is a fluorescent protein.

8. The fusion protein of claim 7, wherein the fluorescent protein is a green fluorescent protein.

9. The isolated protein selected from the group consisting of:
   a) a protein comprising the amino acid sequence of SEQ ID NO: 2, and
   b) a protein encoded by SEQ ID NO: 1.

10. A nucleic acid sequence selected from the group consisting of:
    a) a nucleic acid comprising the nucleotide sequence of SEQ ID NO: 1,
    b) a nucleic acid comprising the complement of SEQ ID NO: 1, and
    c) a nucleic acid which encodes SEQ ID NO: 2.

11. A plasmid or vector that encodes the protein selected from the group consisting of:
    a) a protein comprising the amino acid sequence of SEO ID NO: 2, and
    b) a protein encoded by SEQ ID NO: 1.

12. A cell which expresses the fusion protein selected from the group consisting of:
    a) a protein comprising the amino acid sequence of SEQ ID NO: 2, and
    b) a protein encoded by SEQ ID NO: 1.

13. A replication competent herpesvirus that expresses a fusion protein, wherein the fusion protein comprises:
    a) an ICP8 herpesviral protein, wherein the viral protein has at least one function, and
    b) a fluorescent protein,
       wherein the fluorescent protein and herpesviral protein are fused to maintain an open reading frame and the virus is replication competent and can form a replication compartment.

14. The herpesvirus of claim 13, wherein the fluorescent protein is a green fluorescent protein.

15. A kit comprising the virus of claim 13.

16. The kit of claim 15, further comprising a cell into which the virus can be transfected.

17. The kit of claim 15, further comprising an ICP8 complementing cell line.

18. The replication competent herpesvirus of claim 13, wherein the herpesvirus is a Herpes Simplex virus.

19. The replication competent herpesvirus of claim 13, wherein the herpes virus is selected from the group consisting of: a Herpes Simplex Virus-1, a Herpes Simplex Virus-2, a varicella-zoster virus, a Epstein-Barr Virus, a Cytomegalovirus, a Human Herpesvirus-6, and a Human Herpesvirus-7.

20. A replication competent herpesvirus that expresses a fusion protein, wherein the fusion protein comprises:
    a) an HSV-1 ICP8 viral protein, wherein the HSV-1 ICP8 viral protein retains functions necessary for viral growth in non-complementing cells; and
    b) a fluorescent protein, wherein the HSV-1 ICP8 viral protein and fluorescent protein are fused to maintain an open reading frame.

21. A replication competent herpesvirus that expresses a fusion protein, wherein the fusion protein comprises:
    a) an HSV-1 ICP8 viral protein, wherein the HSV-1 ICP8 viral protein retains functions necessary for replication competence in non-complementing cells; and
    b) a fluorescent protein, wherein the HSV-1 ICP8 viral protein and fluorescent protein are fused to maintain an open reading frame.

22. A replication competent herpesvirus that expresses a fusion protein, wherein the fusion protein comprises:
    a) an ICP8 herpesviral protein, wherein the ICP8 herpesviral protein has at least one function, and
    b) a fluorescent protein,
       wherein the fluorescent protein and herpesviral protein are fused to maintain an open reading frame and the herpesvirus is replication competent.

23. The replication competent herpesvirus of claim 22, wherein the ICP8 heipesviral protein is an HSV-1 viral protein.

24. The replication competent herpesvirus of claim 23, wherein the fluorescent protein is a green fluorescent protein.

* * * * *

UNITED STATES PATENT AND TRADEMARK OFFICE
CERTIFICATE OF CORRECTION

PATENT NO.    : 6,399,354 B1
DATED         : June 4, 2002
INVENTOR(S)   : David M. Knipe, Travis J. Taylor and Elizabeth E. McNamee It is certified that error appears in the above-identified patent and that said Letters Patent is hereby corrected as shown below:

<u>Column 1,</u>
Lines 8-9, under Government Support, delete "Genetics of Herpesvirus Transformation" and insert -- National Institutes of Health --

Signed and Sealed this

Sixth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,399,354 B1  
APPLICATION NO. : 09/127227  
DATED : June 4, 2002  
INVENTOR(S) : Knipe et al.

Page 1 of 1

It is certified that error appears in the above-identified patent and that said Letters Patent is hereby corrected as shown below:

In the Specification

Please delete the paragraph beginning at Column 1, Line number 7 and add the following:
This invention was made with government support under CA026345 awarded by the National Institutes of Health. The government has certain rights in the invention.

This certificate supersedes the Certificate of Correction issued August 6, 2002.

Signed and Sealed this
Seventh Day of January, 2025

Derrick Brent
*Acting Director of the United States Patent and Trademark Office*